(12) United States Patent
Nathan et al.

(10) Patent No.: US 10,080,885 B2
(45) Date of Patent: *Sep. 25, 2018

(54) ORTHOSIS FOR A GAIT MODULATION SYSTEM

(71) Applicant: Bioness Neuromodulation Ltd., Raanana (IL)

(72) Inventors: Roger H. Nathan, Nof-Yam (IL); Amit Dar, Kefar-Hess (IL); Jonathan Bar-Or, Pardes Hanna (IL)

(73) Assignee: Bioness Neuromodulation Ltd., Raanana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/245,597

(22) Filed: Apr. 4, 2014

(65) Prior Publication Data
US 2014/0303705 A1    Oct. 9, 2014

Related U.S. Application Data

(63) Continuation of application No. 13/532,597, filed on Jun. 25, 2012, now Pat. No. 8,694,110, which is a
(Continued)

(51) Int. Cl.
*A61N 1/04*    (2006.01)
*A61N 1/36*    (2006.01)

(52) U.S. Cl.
CPC ......... *A61N 1/0484* (2013.01); *A61N 1/0452* (2013.01); *A61N 1/36003* (2013.01); *A61N 1/36014* (2013.01)

(58) Field of Classification Search
CPC .. A61N 1/0452; A61N 1/0456; A61N 1/0484; A61N 1/36003
See application file for complete search history.

(56) References Cited

U.S. PATENT DOCUMENTS

| 1,422,396 | A | 7/1922 | Wappler |
| 1,644,803 | A | 10/1927 | Wappler |

(Continued)

FOREIGN PATENT DOCUMENTS

| DE | 19830359 A1 | 1/2000 |
| EP | 1508302 | 2/2005 |

(Continued)

OTHER PUBLICATIONS

Supplementary European Search Report for European Application No. 10835019.0, dated Feb. 12, 2014.
(Continued)

*Primary Examiner* — Eric D. Bertram

(57) ABSTRACT

A functional electrical stimulation (FES) orthosis for FES to a limb segment, including: (a) a semi-rigid, self-retaining C-shaped frame, the frame configured to substantially envelop the limb segment, the frame including a first flexible and elongated circumferentially retaining element and at least a first and a second opposing flexible and elongated circumferentially retaining elements disposed on the circumferentially opposite side of the frame, the first retaining element and the first opposing retaining element forming a pair of opposing retaining elements, and (b) a surface electrical stimulation electrode for contacting at least one stimulation point on a surface of the limb segment, associated with, and supported by, the frame, the surface electrode for electrically associating, via the frame, with a neuroprosthetic stimulator unit, so as to provide FES, wherein the opposing retaining elements are configured to be radially spring-loaded towards a center of the frame, such that in donning the orthosis around the limb segment, the limb segment applies a counter-pressure from within the frame, against the opposing retaining elements, such that the ortho-
(Continued)

sis is firmly and fixedly self-retained in a pre-determined position on the surface.

29 Claims, 19 Drawing Sheets

Related U.S. Application Data continuation of application No. 13/036,256, filed on Feb. 28, 2011, now Pat. No. 8,209,036, which is a continuation of application No. 11/380,430, filed on Apr. 27, 2006, now Pat. No. 7,899,556.

(60) Provisional application No. 60/736,858, filed on Nov. 16, 2005.

(56) References Cited

U.S. PATENT DOCUMENTS

| | | | |
|---|---|---|---|
| 3,204,637 A | 9/1965 | Frank et al. | |
| 3,344,792 A | 10/1967 | Offner et al. | |
| 3,426,748 A | 2/1969 | Bowers | |
| 3,881,496 A | 5/1975 | Vredenbregt et al. | |
| 3,941,137 A | 3/1976 | Vredenbregt et al. | |
| 4,381,012 A | 4/1983 | Russek | |
| 4,432,368 A | 2/1984 | Russek | |
| 4,558,704 A | 12/1985 | Petrofsky | |
| 4,580,569 A | 4/1986 | Petrofsky | |
| 4,586,495 A | 5/1986 | Petrofsky | |
| 4,647,918 A | 3/1987 | Goforth | |
| 4,697,808 A | 10/1987 | Larson et al. | |
| 4,745,930 A | 5/1988 | Confer | |
| 4,777,954 A | 10/1988 | Keusch et al. | |
| 4,832,033 A | 5/1989 | Maher et al. | |
| 5,112,296 A | 5/1992 | Beard et al. | |
| 5,116,296 A | 5/1992 | Watkins et al. | |
| 5,121,747 A | 6/1992 | Andrews | |
| 5,253,654 A | 10/1993 | Thomas et al. | |
| 5,277,697 A | 1/1994 | France et al. | |
| 5,285,781 A | 2/1994 | Brodard | |
| 5,323,650 A | 6/1994 | Fullen et al. | |
| 5,330,516 A | 7/1994 | Nathan | |
| 5,350,414 A | 9/1994 | Kolen | |
| 5,357,696 A | 10/1994 | Gray et al. | |
| 5,403,002 A | 4/1995 | Brunty | |
| 5,408,873 A | 4/1995 | Schmidt et al. | |
| 5,437,619 A | 8/1995 | Malewicz et al. | |
| 5,476,441 A | 12/1995 | Durfee et al. | |
| 5,487,759 A | 1/1996 | Bastyr et al. | |
| 5,540,735 A * | 7/1996 | Wingrove | A61F 5/0118 602/21 |
| 5,562,707 A | 10/1996 | Prochazka et al. | |
| 5,613,943 A | 3/1997 | Palumbo | |
| 5,628,722 A | 5/1997 | Solomonow et al. | |
| 5,643,332 A | 7/1997 | Stein | |
| 5,664,346 A | 9/1997 | Barker | |
| 5,724,996 A | 3/1998 | Piunti | |
| 5,748,845 A | 5/1998 | Labun et al. | |
| 5,775,332 A | 7/1998 | Goldman | |
| 5,814,093 A | 9/1998 | Stein | |
| 5,861,017 A | 1/1999 | Smith et al. | |
| 5,916,159 A | 6/1999 | Kelly et al. | |
| 5,951,598 A | 9/1999 | Bishay et al. | |
| 5,980,472 A | 11/1999 | Seyl | |
| 5,983,140 A | 11/1999 | Smith et al. | |
| 6,002,965 A | 12/1999 | Katz et al. | |
| 6,019,877 A | 2/2000 | Dupelle et al. | |
| 6,064,912 A | 5/2000 | Kenney | |
| 6,126,355 A | 10/2000 | Clover, Jr. | |
| 6,129,695 A | 10/2000 | Peters et al. | |
| 6,174,294 B1 | 1/2001 | Crabb et al. | |
| 6,179,799 B1 | 1/2001 | Doran | |
| 6,195,921 B1 | 3/2001 | Truong | |
| 6,246,863 B1 | 6/2001 | Kampel | |
| 6,282,448 B1 | 8/2001 | Katz et al. | |
| 6,308,102 B1 | 10/2001 | Sieracki et al. | |
| 6,349,126 B2 | 2/2002 | Ogawa et al. | |
| 6,438,428 B1 | 8/2002 | Axelgaard et al. | |
| 6,445,955 B1 | 9/2002 | Michelson et al. | |
| 6,456,884 B1 | 9/2002 | Kenney | |
| 6,456,885 B1 | 9/2002 | Shiba et al. | |
| 6,496,739 B2 | 12/2002 | Arbel | |
| 6,507,757 B1 | 1/2003 | Swain et al. | |
| 6,516,500 B2 | 2/2003 | Ogino et al. | |
| 6,564,103 B2 | 5/2003 | Fischer et al. | |
| 6,567,706 B2 * | 5/2003 | Bar-Or | A61N 1/0452 600/391 |
| 6,571,115 B2 | 5/2003 | Axelgaard et al. | |
| 6,578,745 B1 | 6/2003 | Taylor et al. | |
| 6,607,500 B2 | 8/2003 | Da Silva et al. | |
| 6,618,624 B2 | 9/2003 | Elias | |
| 6,651,352 B2 | 11/2003 | McGorry et al. | |
| 6,692,453 B2 | 2/2004 | Wolfe | |
| 6,752,299 B2 | 6/2004 | Shetler et al. | |
| D494,273 S | 8/2004 | Haugland et al. | |
| 6,788,979 B1 | 9/2004 | Axelgaard et al. | |
| 6,829,510 B2 | 12/2004 | Nathan et al. | |
| 6,836,744 B1 | 12/2004 | Asphahani et al. | |
| 6,955,279 B1 | 10/2005 | Mudd et al. | |
| 6,988,005 B2 | 1/2006 | McGraw et al. | |
| 7,011,637 B2 | 3/2006 | Sherman et al. | |
| 7,146,220 B2 | 12/2006 | Dar et al. | |
| 7,158,822 B2 | 1/2007 | Payne, Jr. | |
| 7,162,305 B2 | 1/2007 | Tong et al. | |
| 7,200,517 B2 | 4/2007 | Darley et al. | |
| 7,257,448 B2 | 8/2007 | Crowe et al. | |
| 7,337,007 B2 | 2/2008 | Nathan et al. | |
| 7,359,751 B1 | 4/2008 | Erickson et al. | |
| 7,403,821 B2 | 7/2008 | Haugland et al. | |
| 7,410,471 B1 | 8/2008 | Campbell et al. | |
| 7,416,537 B1 | 8/2008 | Stark et al. | |
| 7,756,585 B2 | 7/2010 | Embrey et al. | |
| 7,785,279 B2 | 8/2010 | Sankai | |
| 7,899,556 B2 * | 3/2011 | Nathan | A61N 1/0484 607/144 |
| 8,070,703 B2 | 12/2011 | Skahan et al. | |
| 8,209,022 B2 * | 6/2012 | Dar | A61B 5/1038 607/144 |
| 8,209,036 B2 * | 6/2012 | Nathan | A61N 1/0484 607/144 |
| 8,382,688 B2 | 2/2013 | Dar et al. | |
| 8,694,110 B2 * | 4/2014 | Nathan | A61N 1/0484 607/48 |
| 8,788,049 B2 | 7/2014 | Lasko et al. | |
| 8,868,217 B2 | 10/2014 | Dar et al. | |
| 8,972,017 B2 * | 3/2015 | Dar | A61B 5/1038 607/144 |
| 9,095,417 B2 | 8/2015 | Dar et al. | |
| 2002/0077688 A1 | 6/2002 | Kirkland | |
| 2003/0040788 A1 | 2/2003 | Dupelle et al. | |
| 2003/0050673 A1 | 3/2003 | Yamakazi et al. | |
| 2003/0065368 A1 | 4/2003 | Van Der Hoeven | |
| 2003/0083596 A1 | 5/2003 | Kramer et al. | |
| 2003/0114892 A1 | 6/2003 | Nathan et al. | |
| 2003/0114893 A1 * | 6/2003 | Nathan | A61N 1/0452 607/48 |
| 2003/0114894 A1 | 6/2003 | Dar et al. | |
| 2003/0171706 A1 | 9/2003 | Nelson | |
| 2004/0011366 A1 | 1/2004 | Schulman et al. | |
| 2004/0122483 A1 | 6/2004 | Nathan et al. | |
| 2004/0147975 A1 | 7/2004 | Popovic et al. | |
| 2004/0172097 A1 | 9/2004 | Brodard et al. | |
| 2004/0173220 A1 | 9/2004 | Harry et al. | |
| 2004/0236384 A1 * | 11/2004 | Dar | A61N 1/0452 607/48 |
| 2004/0243197 A1 | 12/2004 | Demian | |
| 2004/0254624 A1 | 12/2004 | Johnson | |
| 2005/0043660 A1 | 2/2005 | Stark et al. | |
| 2005/0049652 A1 | 3/2005 | Tong | |
| 2005/0085706 A1 | 4/2005 | Perrault et al. | |
| 2005/0131317 A1 | 6/2005 | Oddsson et al. | |
| 2005/0192645 A1 | 9/2005 | Stein et al. | |
| 2005/0261609 A1 | 11/2005 | Collings et al. | |

(56) References Cited

U.S. PATENT DOCUMENTS

| | | | |
|---|---|---|---|
| 2006/0015470 | A1 | 1/2006 | Lauer et al. |
| 2006/0211956 | A1 | 9/2006 | Sankai |
| 2006/0276704 | A1 | 12/2006 | McGinnis et al. |
| 2006/0282017 | A1 | 12/2006 | Avni et al. |
| 2006/0282018 | A1 | 12/2006 | Balzano |
| 2007/0021689 | A1 | 1/2007 | Stergiou et al. |
| 2007/0106343 | A1* | 5/2007 | Monogue ............ A61B 5/0492 607/48 |
| 2007/0112285 | A1 | 5/2007 | Dar et al. |
| 2007/0112394 | A1 | 5/2007 | Nathan et al. |
| 2007/0179560 | A1 | 8/2007 | Tong et al. |
| 2007/0197946 | A1 | 8/2007 | Gilmour |
| 2007/0203533 | A1 | 8/2007 | Goren et al. |
| 2008/0033505 | A1 | 2/2008 | Davis et al. |
| 2008/0045872 | A1 | 2/2008 | Bauerfeind et al. |
| 2008/0046036 | A1 | 2/2008 | King et al. |
| 2008/0140154 | A1 | 6/2008 | Loeb et al. |
| 2008/0154113 | A1 | 6/2008 | Zilberman |
| 2008/0154335 | A1 | 6/2008 | Thrope et al. |
| 2008/0319349 | A1 | 12/2008 | Zilberman |
| 2009/0012436 | A1 | 1/2009 | Lanfermann et al. |
| 2009/0043357 | A1 | 2/2009 | Tong et al. |
| 2009/0069865 | A1 | 3/2009 | Lasko et al. |
| 2009/0177131 | A1 | 7/2009 | Dar et al. |
| 2011/0137375 | A1 | 6/2011 | McBride |
| 2011/0152968 | A1 | 6/2011 | Nathan et al. |
| 2012/0059432 | A1 | 3/2012 | Emborg et al. |
| 2012/0203156 | A1 | 8/2012 | Dar et al. |
| 2012/0330375 | A1 | 12/2012 | Nathan et al. |
| 2012/0330394 | A1 | 12/2012 | Dar et al. |
| 2012/0330395 | A1 | 12/2012 | Dar et al. |
| 2013/0131555 | A1 | 5/2013 | Hook et al. |
| 2014/0180361 | A1 | 6/2014 | Burdick et al. |
| 2015/0080979 | A1 | 3/2015 | Lasko et al. |
| 2015/0265834 | A1 | 9/2015 | Glukhovsky et al. |
| 2015/0273205 | A1 | 10/2015 | Dar et al. |
| 2015/0321000 | A1 | 11/2015 | Rosenbluth et al. |
| 2017/0065815 | A1 | 3/2017 | Lasko et al. |

FOREIGN PATENT DOCUMENTS

| | | |
|---|---|---|
| JP | 1985-119949 A | 6/1985 |
| JP | 1994-501854 T | 3/1994 |
| JP | 2002-191580 A | 7/2002 |
| JP | 2004-503266 T | 2/2004 |
| JP | 2004-215735 A | 8/2004 |
| JP | 2004-313555 A | 11/2004 |
| JP | 2005-514143 T | 5/2005 |
| JP | 2006-166244 A | 6/2006 |
| JP | 2009-530064 | 8/2009 |
| WO | WO 2003/051453 | 6/2003 |
| WO | WO 2004/098703 | 11/2004 |
| WO | WO 2006/113801 | 10/2006 |
| WO | WO 2008/005865 | 1/2008 |
| WO | WO 2014/030295 | 2/2014 |

OTHER PUBLICATIONS

Office Action for U.S. Appl. No. 12/630,199, dated Jun. 21, 2011.
International Search Report and Written Opinion for International Application No. PCT/US2010/058483, dated Feb. 7, 2011.
Examination Report for Australian Application No. 2006314072, dated May 5, 2010, 4 pages.
Examination Report for Australian Application No. 2006314072, dated Jul. 5, 2011, 2 pages.
Office Action for Canadian Application No. 2,632,196, dated Mar. 16, 2010, 4 pages.
Supplementary European Search Report for European Application No. 06821561.5, dated Dec. 16, 2013.
Office Action for Korean Patent Application No. 10-2008-7014295, dated Oct. 28, 2010.
Office Action for U.S. Appl. No. 12/096,077, dated Apr. 5, 2012, 10 pages.
Office Action for Canadian Application No. 2,794,533, dated Nov. 29, 2013, 3 pages.
Office Action for U.S. Appl. No. 13/532,603, dated Nov. 29, 2013.
Office Action for U.S. Appl. No. 11/380,430 dated Mar. 5, 2009.
Office Action for U.S. Appl. No. 11/380,430, dated Nov. 13, 2009, 8 pages.
Office Action for U.S. Appl. No. 11/380,430, dated Mar. 24, 2010, 12 pages.
Office Action for U.S. Appl. No. 11/380,430, dated Sep. 1, 2010, 11 pages.
International Search Report for PCT/IL06/01326, dated Oct. 13, 2009.
Office Action for Australian Patent Application No. AU 2007245258, dated Apr. 12, 2012.
Examination Report for European Application No. 07736271.3, dated Nov. 14, 2011.
Notice of Reasons for Rejection for Japanese Patent Application No. 2009-517597, dated Jan. 23, 2012.
International Preliminary Report on Patentability for PCT/IL07/00531, dated Mar. 10, 2009.
International Search Report for PCT/IL07/00531, dated Jul. 7, 2008.
Office Action for U.S. Appl. No. 12/631,095, dated Sep. 14, 2011.
Office Action for U.S. Appl. No. 13/036,256, dated Apr. 5, 2012, 8 pages.
Office Action for U.S. Appl. No. 13/532,597, dated Apr. 23, 2013.
Office Action for U.S. Appl. No. 13/169,553, dated Apr. 29, 2013.
Office Action for U.S. Appl. No. 13/169,553, dated Sep. 17, 2013.
International Search Report and Written Opinion for International Application No. PCT/IL2012/000260, dated Oct. 9, 2012, 13 pages.
Office Action for U.S. Appl. No. 13/022,149, dated Jan. 15, 2013.
Office Action for U.S. Appl. 13/022,149, dated Jul. 15, 2013.
Supplementary European Search Report for European Application No. 12745088.0, dated Jun. 6, 2014.
International Search Report and Written Opinion for International Application No. PCT/IL2012/000063, dated Jun. 29, 2012, 11 pages.
International Search Report and Written Opinion for International Application No. PCT/US2015/020992, dated Jun. 24, 2015.
Alon, G. et al., "Persons with C5 or C6 tetraplegia achieve selected functional gains using a neuroprosthesis," Arch. Phys. Med. Rehabil., 84:119-124 (Jan. 2003).
"Clinical evaluation of the ljubljana functional electrical peroneal brace," Subcommittee on Evaluation, Committee on Prosthetics Research and Development Division of Medical Sciences—National Research Council, National Academy of Sciences, Washington, D.C., Report E-7 (1973).
Daly, W. K., "Electrodes installed in roll-on suspension sleeves," From "MEC '02 The Next Generation," Proceedings of the 2002 MyoElectric Controls/Powered Prosthetics Symposium, Fredericton, New Brunswick, Canada: Aug. 21-23, 2002, University of New Brunswick, 3 pages.
Davis, R. et al., "Evaluation of electrical stimulation as a treatment for the reduction of spasticity," Bulletin of Prosthetics Research, Department of Medicine and Surgery Veterans Administration, Washington, D.C., pp. 302-309 (1974).
Duncan, R. M., "Basic principles of splinting the hand," Journal of the American Physical Therapy Association, 69(12):1104-1116 (1989).
Hart, R. L. et al., "A comparison between control methods for implanted FES hand-grasp systems," IEEE Transactions on Rehabilitation Engineering, 6(2):208-218 (Jun. 1998).
Hendricks, H. T. et al., "Functional electrical stimulation by means of the 'Ness Handmaster Orthosis' in chronic stroke patients: an exploratory study," Clinical Rehabilitation, 15:217-220 (2001).
Kralj, A. et al., "Functional electrical stimulation of the extremities: part 1," Journal of Medical Engineering and Technology, pp. 12-15 (Jan. 1977).
Kralj, A. et al., "Functional electrical stimulation of the extremities: part 2," Journal of Medical Engineering and Technology, pp. 75-80 (Mar. 1977).
Kralj, A. R. et al., "Functional Electrical Stimulation: Standing and Walking after Spinal Cord Injury," CRC Press, Boca Raton, FL., pp. 1-15 (1989).

(56) References Cited

OTHER PUBLICATIONS

Liberson, W. T. et al., "Functional Electrotherapy: Stimulation of the Peroneal Nerve Synchronized with the Swing Phase of the Gait of Hemiplegic Patients," Archives of Physical Medicine & Rehabilitation, pp. 101-105 (Feb. 1961).
NDI Medical, "About ODFS Dropped Foot Stimulator," [online] 2005 [retrieved on Jun. 5, 2006]. Retrieved from the Internet: URL: <http://www.odfs.com/About_ODFS/about_odfs.html>.
NESS H200 Product Specifications "H200™ Overview& Product Specifications," [online] 2006 [retrieved on Jun. 5, 2007]. Retrieved from the Internet: URL: <http://www.bionessinc.com/products/h200/htm>.
Neurodan, "ActiGait® An implantable drop foot correction system," Neurodan A/S—Products—ActiGait® [online] [retrieved on Jun. 5, 2007]. Retrieved from the Internet: URL: <http://www.neurodan.com/actigait.asp>.
NMES Guidelines for Treatment "Gait Training," [online] [retrieved on May 30, 2007]. Retrieved from the Internet: URL: <http://www.empi.com/products1nmes/gait.pdf>.
Popovic, M. R. et al., "Neuroprostheses for grasping," Neurological Research, 24:443-452 (Jul. 2002).
Popovic, M. R. et al., "Functional electrical therapy: retraining grasping in spinal cord injury," Spinal Cord, 44:143-151 (2006).
Prochazka, A. et al., "The bionic glove: An electrical stimulator garment that provides controlled grasp and hand opening in quadriplegia," Arch. Phys. Med. Rehabil., 78:608-614 (Jun. 1997).
Senelick, R. C., "Technological Advances in Stroke Rehabilitation-High Tech Marries High Touch," US Neurology, 6(2):102-104 (2010), Extract (Touch Group PLC, 4 pages).
Sowerbutt, C., "Restoring Gait in Stroke Patients Using Functional Neuromuscular Stimulation," [online] Sep. 1, 2006 [retrieved on May 30, 2007]. Retrieved from the Internet: URL: <http://appneurology.com/showArticle.jhtml?print=true&articleID=193104432>.
Stanic, U., "History of functional electrical stimulation," International Functional Electrical Stimulation Society, INS & IFESS Joint Congress, Sep. 16-20, 1998, Lucerne, Switzerland, 37 pages.
Stopar, M. et al., "New stimulators for cutaneous stimulation," Advances in External Control of Human Extremities, Proceedings of the Seventh International Symposium on External Control of Human Extremities, pp. 267-272 (1981).
Stralka, "Gait Training (by Stimulating Dorsiflexors)," NM III™ Neuromuscular Stimulation System Suggested Protocol, NM III Program Set #2 Program F, Rehabilicare® 920080 Rev. C.
Strojnik, P. et al., "Treatment of drop foot using an implantable peroneal underknee stimulator," Scandanavian J. of Rehabil. Med. 19:37-43 (1987).
Strojnik, P. et al., "Implantable stimulators for neuromuscular control," Chapter 78 in the Biomedical Engineering Handbook: Second Edition, Bronzino, J. D. (ed.), Boca Raton: CRC Press LLC (2000), 15 pages.
Uellendahl, J. E. et al., "Custom silicone sockets for myoelectric prostheses," Journal of Prosthetics and Orthotics, 18(2):35-40 (2006).
Uellendahl, J. E. et al., "Custom silicone sockets for myoelectric prostheses," From "MEC '05 Intergrating Prosthetics and Medicine," Proceedings of the 2005 MyoElectric Controls/Powered Prosthetics Symposium, held in Fredericton, New Brunswick, Canada, Aug. 17-19, 2005, 6 pages.
Vodovnik, L. et al., "Functional electrical stimulation for control of locomotor systems," CRC Critical Reviews in Bioengineering, 6(2):63-131 (Sep. 1981).
Ward, A. R. et al., "Russian electrical stimulation: The early experiments," Physical Therapy, 82(10):1019-1030 (Oct. 2002).
Waters, R. L. et al.: "Effectiveness of selected surface electrodes for motor stimulation," Advances in External Control of Human Extremities, Proceedings of the Sixth International Symposium on External Control of Human Extremities, pp. 31-38 (1978).
Waters, R. L. et al., "Experimental correction of footdrop by electrical stimulation of the peroneal nerve," J Bone Joint Surg Am., vol. 38, No. 8 (Dec. 1975), pp. 1047-1054.
Waters, R. et al., "Treatment of the hemiplegic upper extremity using electrical stimulation and biofeedback training," Report to the Veterans Administration, Contract V600P-1064-79, Funding Period Sep. 27, 1979-Sep. 30, 1980, pp. 251-266.
Wood, D.E., "Spatial sensitivity comparisons between an implanted and surface dropped foot neuromuscular stimulator," 9th Annual Conference of the International FES Society, Sep. 2004.
Patent Examination Report No. 1 for Australian Application No. 2013260668, dated Jan. 4, 2016, 4 pages.
Examination Report No. 1 for Australian Application No. 2015201998, dated Oct. 26, 2017, 7 pages.
Office Action for U.S. Appl. No. 14/636,628, dated Nov. 14, 2017, 16 pages.
Supplementary European Search Report and Opinion for European Application No. 15770404.0, dated Oct. 19, 2017, 8 pages.
Williamson, R. et al., "Sensor systems for lower limb functional electircal stimulation (FES) control," Medical Engineering and Physics, 2000, vol. 22, pp. 313-325.
Office Action for Canadian Application No. 2,930,077, dated Sep. 11, 2017, 3 pages.
Office Action for Australian Application No. 2017202373, dated Jan. 4, 2018, 4 pages.
Office Action for U.S. Appl. No. 14/223,340, dated Jun. 16, 2016, 10 pages.
Office Action for U.S. Appl. No. 14/223,340, dated Jan. 11, 2017, 9 pages.
International Search Report and Written Opinion for International Application No. PCT/US2017/012977, dated Mar. 17, 2017, 12 pages.
Bogataj, U. et al., "Preliminary testing of a dual-channel electrical stimulator for correction of gait," Journal of Rehabilitation Research and Development, vol. 24, No. 3, pp. 75-80, Summer 1987. Retrieved from the Internet: Dec. 29, 2016, <URL: http://www.rehab.research.va.gov/jour/87/24/3/pdf/bogataj.pdf>.
Shenzhen XFT Electronics Co., Ltd., Foot Drop System, XFT-2001 User Manual, 16 pages. Retrieved from the Internet: Aug. 10, 2016, <URL: http://www.stressnomore.co.uk/downloads/instructions/91846-IFUS_1.pdf>.

* cited by examiner

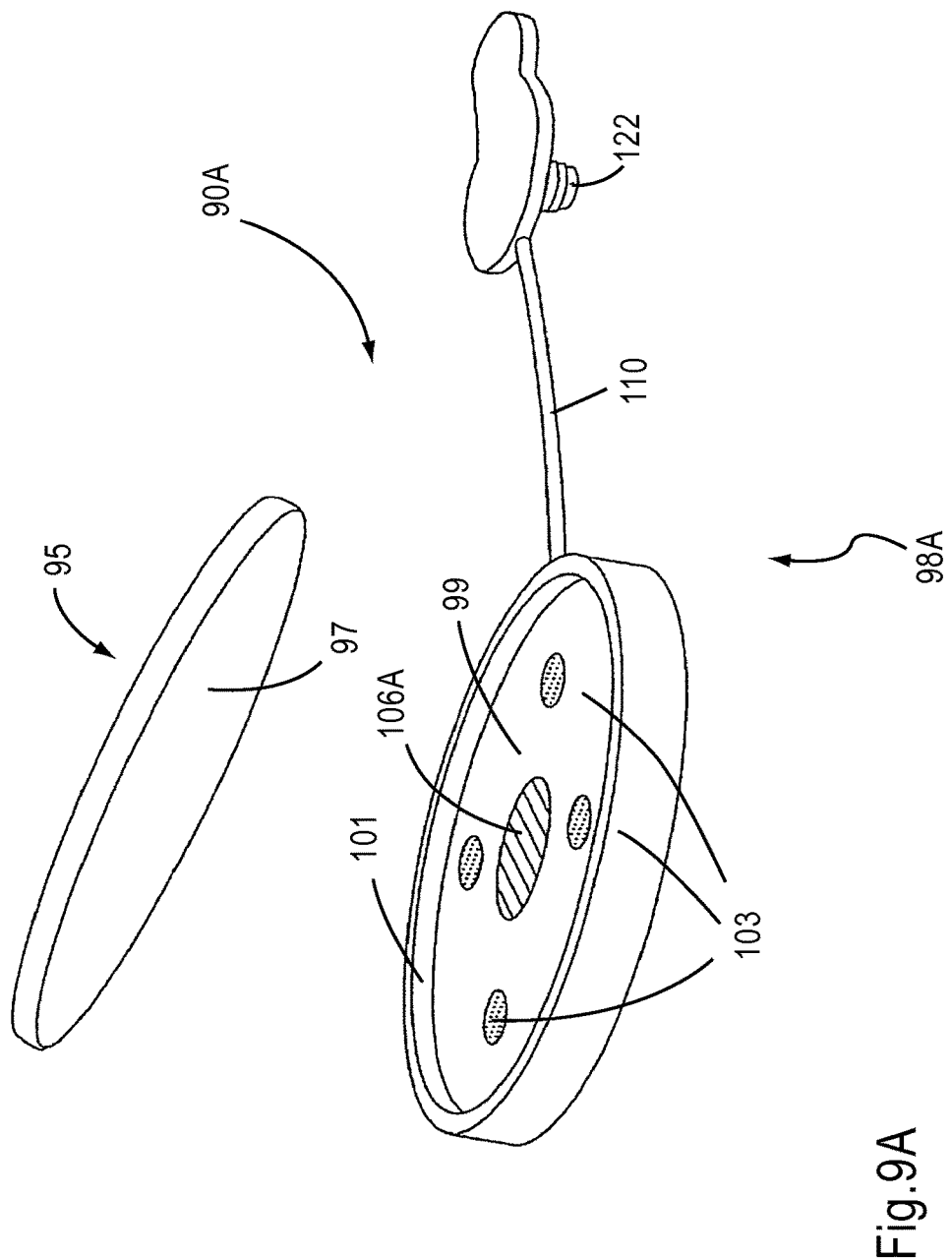

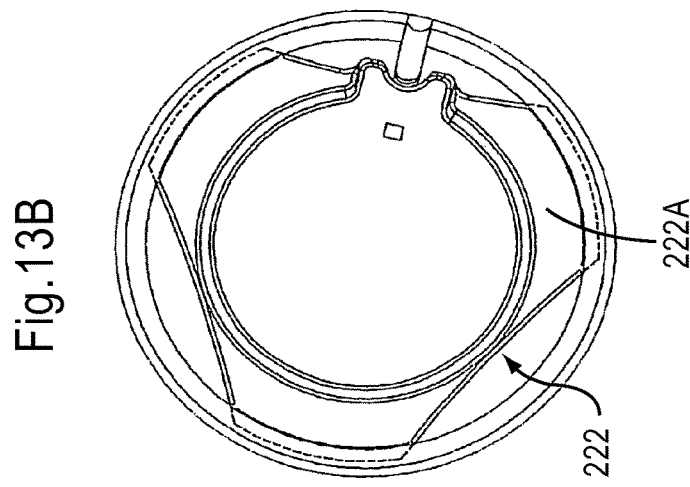
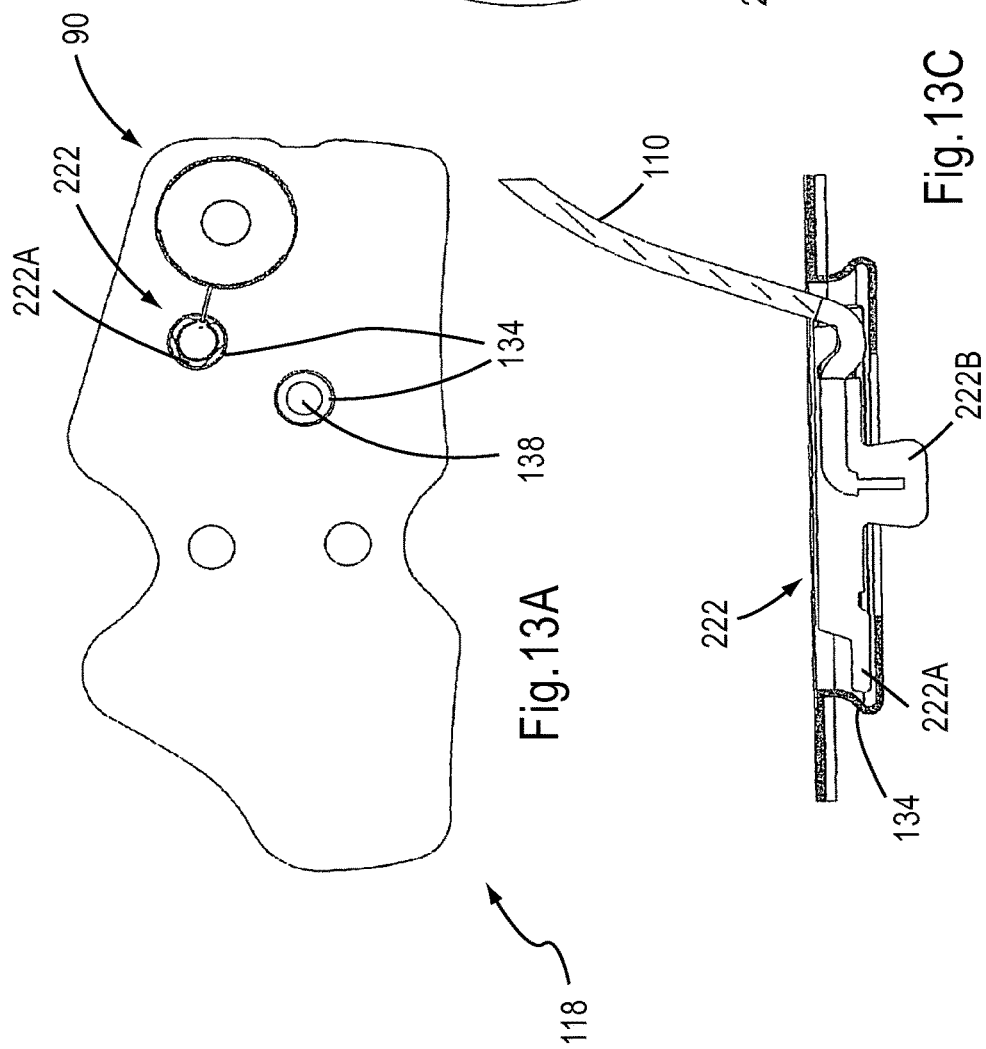

ORTHOSIS FOR A GAIT MODULATION SYSTEM

CROSS-REFERENCE TO RELATED APPLICATIONS

This application is a continuation of U.S. application Ser. No. 13/532,597, now U.S. Pat. No. 8,694,110, entitled "Orthosis for Gait Modulation," filed Jun. 25, 2012, which is a continuation of U.S. application Ser. No. 13/036,256, now U.S. Pat. No. 8,209,036, entitled "Orthosis for a Gait Modulation System," filed Feb. 28, 2011, which is a continuation of U.S. application Ser. No. 11/380,430, now U.S. Pat. No. 7,899,556, entitled "Orthosis for a Gait Modulation System," filed Apr. 27, 2006, which claims priority to U.S. Provisional Patent Application Ser. No. 60/736,858, filed Nov. 16, 2005, each of which is incorporated herein by reference in its entirety.

BACKGROUND

The present invention relates to gait modulation systems using functional electrical stimulation (FES), and more particularly, to an FES orthosis for such an FES orthosis and method of using such gait modulation systems.

It is known that pathologies of the neuromuscular system due to disease or trauma to the central nervous system, such as stroke, spinal cord injury, head injury, cerebral palsy and multiple sclerosis, can impede proper limb functioning of the hands or legs. Gait, the biomechanical description of walking, can suffer static and dynamic parameter variations due to neuromuscular impairments, which cause non-symmetrical walking, reduced walking speed and reduced walking stability.

Drop foot describes the gait attributable to weak or uncoordinated activation of the ankle dorsi-flexors due to disease or trauma to the central nervous system. Patients suffering from drop foot tend to drag the foot during the swing phase of walking and usually try to compensate for this dragging by hiking their hip or swinging it in a circular motion. These patients tend to have impaired stability, are prone to frequent falls, and their walking movements are unaesthetic and energy consuming.

However, limb muscles can generally be activated with FES. In FES, precisely timed bursts of short electrical pulses are applied to motor nerves, to generate muscle contraction, which can be applied to enhancing limb function.

Although more than four decades have elapsed since the first neuroprosthetic system was proposed, much room remains for improving the technological quality of such systems. This is reflected, inter alia, by the relatively small percentage of potential users who regularly don a neuroprosthetic device to compensate for limb and gait problems, and particularly, a drop foot problem. These systems suffer from many drawbacks that prevent them from being widely used by potential patients.

When problems with arm movement or gait result from stroke or brain injury, they are often accompanied by hand impairment on the same side of the body as the limb on which the FES orthosis is donned. Thus, the donning action must often be carried out using solely the contra-lateral, unaffected hand. Moreover, the posture of the plegic limb is often problematic, especially in cases where spasticity results in reduced voluntary movements and also in a limited passive range of motion of the limb joints. Consequently, objective biomechanical problems exist in donning the orthotic device and in locating the electrodes in exact position onto the limb. Prior art neuroprosthetic devices differ in that they fail to enable facile, quick and accurate donning of the device by an impaired patient using a single hand, and particularly, when even that hand is shaky or otherwise unstable.

Prior art external FES devices typically utilize a stimulator unit that is physically separate from the FES orthosis, to create and control the electrical pulses being applied to motor nerves. The external stimulator unit, which is connected to the FES orthosis by several electrical wires, is located on the body of the user, and is typically attached to the belt of the user. These devices can be inconvenient for the user. Particularly cumbersome is the wiring, which is usually arranged to run along the leg under the clothing to connect the device components.

In additional, neuroprostheses require precise fitting for each individual patient, in an optimal fashion, by exactly identifying the stimulation points that cause contraction of the muscles, and positioning and locking the electrodes thereto. Consequently, use of the known devices, which are configured and dedicated to the anatomy and needs of a particular individual, is limited to that individual only, and further requires considerable expertise to reconfigure the device for transfer to another patient.

U.S. Pat. Nos. 5,643,332 and 5,814,093 to Stein disclose an assembly for functional electrical stimulation during movement, including a band, mountable on the leg, carrying all of the components of the assembly to provide a self-contained unit. The components comprise: electrodes for stimulating a leg nerve; a V-shaped plate for conforming with the leg's tibia to reproducibly position the band so that the electrodes are located over the nerve; a tilt sensor for measuring the angular position of the lower leg; a control circuit for processing the sensor signal information and emitting pulses through the electrodes to stimulate the leg in response to phases of body movement; and a battery for supplying power to the tilt sensor, control circuit and stimulator. The disclosed band is made of stretchable, breathable material.

WalkAide™ is a commercially available FES device of Innovative Neurotronics, Inc., and is based on the technology disclosed by Stein. The orthosis component of the WalkAide™ is a narrow band made of a thermoplastic material that is molded to the limb anatomy of an individual user by heating and softening the thermoplastic material and subsequently fitting the contour to the contour of the underlying limb segment. Thus the shape and size of the device and the electrode positioning is custom-fitted to the leg of one user and individualized for the user. This procedure is carried out by a trained medical professional.

For a clinic or rehabilitation center serving a large number of users, it would be advantageous a device that can be transferred from patient to patient hygienically and with facility. Neuroprosthetic devices require a significant and time-consuming set-up procedure carried out by a trained medical professional to fit the device to the anatomy of the limb, position the electrodes accurately over the motor point, and adjust the stimulation parameters when transferring the device to another patient. Parts of the orthosis are in prolonged contact with the skin during a session of use, and existing devices have no provision for hygienically passing the orthosis from the leg of one patient on to another.

Prior art orthosis-based devices for the leg such as the WalkAide™ device operate with relatively small electrodes typically having a diameter of 25 mm and a surface area in contact with the skin of about 4.9 $cm^2$ positioned relatively close together in the orthosis. This enables the orthosis to take the form of a relatively narrow band to accommodate the small electrodes and separation. However, activation of the leg muscles by electrical stimulation requires typically high stimulation currents. But the stimulation current passing through the electrode to the skin surface activates skin sensory receptors in addition to underlying excitable motor nerve and muscle tissue and the intensity of sensory activation will depend on the intensity of the current density passing through the skin surface. The level of muscle activation is often limited in the typical patient by his individual tolerance to activation of these skin pain sensors. For these patients, it would be advantageous to reduce the sensory discomfort by lowering the skin current density while maintaining levels of muscle activation. A further means to increase the contraction force of the activated muscles is to increase the distance separating the electrodes in the pair, particularly the distance along the length of the leg. This can result in the recruitment of more muscle fibers, resulting in increased activated rotation torque output from the ankle joint, without the necessity to use a high stimulation current intensity. This electrode geometry and arrangement for increasing muscle force output and reducing sensory discomfort is too large to fit within the prior art narrow band design of the orthosis. To date, no orthosis exists for accommodating surface electrodes of such size and configuration.

Furthermore, a means for accurately positioning the electrodes along the length of the leg becomes essential where the electrodes are significantly separated in this longitudinal direction, and accurate longitudinal positioning of the orthosis becomes mandatory to avoid activating unwanted muscles. Accommodating the large stimulation electrodes with a larger distance separating them particularly in the longitudinal direction requires housing these electrodes in an orthosis that is significantly wider, extending both proximally and distally along the length of the leg. The wide orthosis design introduces new problems concerned with fitting and self-placement. Moreover, the larger dimensions of the orthosis appreciably compromise the ability of the orthosis to fit the contour of the limb segment, especially during limb extensions, flexions and gait.

Also, an accurate but simple means to enable the typical stroke patient to position the height of the orthosis along the length of the leg is required. Prior art leg devices have used anatomical landmarks such as the tibia as a reference to locate the device orthosis on to the leg. The wide orthosis design is difficult to locate on to the tibia. Especially in large and wide legs, the tibial crest is rather flat and consequently is a poor anatomical landmark for accurately positioning the orthosis and hence the electrodes circumferentially around the leg. Moreover, the longitudinal positioning along the leg is not positively determined by the tibial crest.

There is therefore a recognized need for, and it would be highly advantageous to have, an improved FES orthosis for a neuroprosthetic system and method that overcome the manifest deficiencies of the prior art. It would be of particular advantage to have an FES leg orthosis that can easily and accurately be donned on the limb by patients also suffering from an impaired hand. It would also be of particular advantage to have an FES leg orthosis in which an even pressure of the electrode surface is maintained during limb extensions, flexions and gait. It would also be of particular advantage to enable greater ankle torque generation with lessening of skin sensory discomfort at the electrode site by increasing the size and longitudinal separation of the electrodes. It would be of further advantage for the FES orthosis to be substantially universally adaptable to the different anthropometric variables of limbs and to electrode positioning needs of a wide variety of users. Finally, it would be of particular advantage to have an FES orthosis designed and configured such that the on-board stimulation unit does not significantly protrude outside the profile of the orthosis and does not impede donning and wearing clothing such as trousers over the orthosis. This is of Major significance to the stroke patient who is generally is challenged by donning trousers on to his plegic leg using a single hand, and a protruding device attached to his leg may disable his ability to dress himself independently.

SUMMARY

According to the teachings of the present invention there is provided a functional electrical stimulation orthosis for providing functional electrical stimulation to a limb segment of a user, the orthosis including: (a) an at least semi-rigid, self-retaining C-shaped frame, the frame configured to substantially envelop the limb segment, the frame including a first flexible and elongated circumferentially retaining element and at least a first and a second opposing flexible and elongated circumferentially retaining elements disposed on the circumferentially opposite side of the frame, the first retaining element and the first opposing retaining element forming a pair of opposing retaining elements, and (b) at least one surface electrical stimulation electrode for contacting at least one stimulation point on a surface of the limb segment, associated with, and supported by, the frame, the at least one surface electrode for electrically associating, via the frame, with a neuroprosthetic stimulator unit, so as to provide functional electrical stimulation, wherein the opposing retaining elements are configured to be radially spring-loaded towards a center of the frame, such that in donning the orthosis around the limb segment, the limb segment applies a counter-pressure from within the frame, against the opposing retaining elements, such that the orthosis is firmly and fixedly self-retained in a pre-determined position on the surface of the limb segment.

According to further features in the described preferred embodiments, all of the flexible and elongated retaining elements are configured to conform to a contour of the surface in a substantially independent fashion, so as to maintain intimate contact with the contour.

According to still further features in the described preferred embodiments, the opposing retaining elements include at least three flexible and elongated circumferentially retaining elements.

According to still further features in the described preferred embodiments, the orthosis further includes: (c) a locking mechanism, associated with the frame, for locking the at least one surface electrical stimulation electrode at the pre-determined position on the surface of the limb segment.

According to still further features in the described preferred embodiments, the opposing retaining elements are designed and configured to independently respond, mechanically, to changes in the contour, so as to retain the at least one surface electrical stimulation electrode fixed against the pre-determined position on the limb segment and so as to maintain an even pressure against the pre-determined position on the surface of the limb segment.

According to still further features in the described preferred embodiments, the semi-rigid frame includes a housing for receiving the stimulator unit.

According to still further features in the described preferred embodiments, the housing is dimensioned to envelop and hold the stimulator unit intimately and flatly against the orthosis.

According to still further features in the described preferred embodiments, the orthosis further includes: (c) the neuroprosthetic stimulator unit, wherein the stimulator unit is designed and configured to: (i) communicate with a sensor for sensing a physical parameter relating to the limb segment, and (ii) based on a signal relating to the sensor, deliver a stimulation signal to the surface electrode.

According to still further features in the described preferred embodiments, the stimulator unit includes a radio frequency transceiver for communicating with at least one of a stimulator control unit and the sensor.

According to still further features in the described preferred embodiments, the locking mechanism includes at least one elastic strap designed to extend circumferentially around and bridge between the opposite sides of the frame and to be reversibly fastened to a fastening element associated with the frame.

According to still further features in the described preferred embodiments, the orthosis is a lower-leg orthosis, wherein an upper contour of the orthosis is a locating surface, the locating surface configured to conform to an inferior border of a patella of the user.

According to still further features in the described preferred embodiments, the locating surface has a three-dimensional cup shape for abutting an inferior border of a patella of the user during donning of the orthosis.

According to still further features in the described preferred embodiments, the orthosis is designed and configured for single-handed donning by the user.

According to still further features in the described preferred embodiments, the fastening element includes a protuberance associated with the frame.

According to still further features in the described preferred embodiments, the protuberance includes a housing for receiving the stimulator unit.

According to still further features in the described preferred embodiments, the at least one elastic strap terminates in a looped handle, the looped handle designed to be reversibly fastened to the fastening element.

According to still further features in the described preferred embodiments, the orthosis further includes: (c) the neuroprosthetic stimulator unit, and (d) a housing for receiving the stimulator unit, the housing disposed on a flexible leaf on the frame, such that the housing and the leaf are free to move as a unit, independently of the retaining elements, so as enable the retaining elements to mechanically respond, substantially independently, to changes in a contour of the leg segment, even when pressure is exerted on an exterior face of the stimulator unit.

According to still further features in the described preferred embodiments, circumferentially disposed on the frame is at least one spring-loaded strip, the strip being radially spring-loaded towards a center of the frame, such that in donning the orthosis around the limb segment, the spring-loaded strip applies a pressure against the limb segment, such that the orthosis is self-retained in position on the limb segment while allowing for small adjustments to be made in positioning of the orthosis on the limb segment.

According to still further features in the described preferred embodiments, the second flexible and elongated circumferentially retaining element has a width, W, wherein W is within a range of about 2-4.5 cm.

According to still further features in the described preferred embodiments, the second opposing retaining element has a width, W, and the orthosis has a height, H, and wherein W is within a range of 8-60% of H.

According to still further features in the described preferred embodiments, each of the at least one surface electrical stimulation electrode has a surface area for contacting the surface of the limb segment, and wherein for each the electrode, the surface area is at least 9 $cm^2$.

According to still further features in the described preferred embodiments, the surface area is at least 12 $cm^2$.

According to still further features in the described preferred embodiments, the at least one elastic strap terminates in a looped handle, the looped handle designed to be reversibly fastened to the fastening element, and wherein the looped handle, when fastened to the fastening element, completes a smooth and substantially non-protruding profile that includes the orthosis, the stimulator unit, the housing, and the looped handle, all of which together blend into a profile of a leg of the user.

According to yet another aspect of the present invention there is provided an orthosis of for providing functional electrical stimulation to a limb segment of a user, the orthosis including: (a) an at least semi-rigid frame being configured to substantially envelop the limb segment; (b) a soft inner facing for at least partially covering an inner face of the frame and for providing a comfortable interface between the frame and the limb segment; (c) a first mechanical fitting associated with the inner face of said frame, and (d) at least one surface electrical stimulation electrode assembly associated with, and supported by the frame, the assembly having a stimulation electrode having a surface for contacting at least one stimulation point on the limb segment, and an attachment mechanism for fixing a position of the electrode with respect to the frame, the at least one surface electrode for electrically associating, by way of the frame, with a neuroprosthetic stimulator unit for providing a stimulation signal to the surface electrode, and wherein the stimulation electrode assembly has a second mechanical fitting, complementary to the first mechanical fitting, for reversibly attaching the stimulation electrode assembly to, and reversibly detaching the stimulation electrode assembly from, the first mechanical fitting.

According to still further features in the described preferred embodiments, the first and second mechanical fittings are connectors selected from the group consisting of snaps and hook and loop fasteners.

According to still further features in the described preferred embodiments, the attachment mechanism includes an electrode base having a surface for receiving and engaging a second side of the stimulation electrode, the second side being opposite the first side.

According to still further features in the described preferred embodiments, the electrode base has a rim for physically defining, for the stimulation electrode, a substantially singular position therein.

According to still further features in the described preferred embodiments, the second side of the stimulation electrode includes a hydrogel-containing surface, and wherein the surface of the electrode base includes at least one patch of hook fasteners for securing the hydrogel-containing surface to the electrode base.

According to still further features in the described preferred embodiments, the soft inner facing is a reversibly attachable and detachable panel.

According to still further features in the described preferred embodiments, the orthosis further includes: (e) a soft panel for covering at least a portion of the soft inner facing, the soft panel having a third complementary connector for associating with a fourth complementary connector associated with the frame, so as to reversibly secure the soft panel to the frame.

According to another aspect of the present invention there is provided an orthosis for providing functional electrical stimulation to a limb segment of a user, the orthosis including: (a) an at least semi-rigid frame configured to substantially envelop the limb segment, the frame having at least one first complementary mechanical fastener associated therewith; (b) at least one surface electrical stimulation electrode assembly associated with, and supported by the frame, the assembly having a surface stimulation electrode for contacting at least one stimulation point on the limb segment, the at least one surface electrode assembly having an electrode base for electrically associating, via the frame, with a neuroprosthetic stimulator unit for providing a stimulation signal to the surface electrode, the electrode base having a top face for receiving the stimulation electrode, the electrode base having a bottom face having at least one second complementary mechanical fastener, the second fastener being complementary to the first fastener, the first and second fasteners designed and configured for reversible attachment and reversible detachment, at a plurality of locations on the frame, thereby enabling the electrical stimulation electrode assembly to be adjustably and reversibly positioned on the frame.

According to further features in the described preferred embodiments, the electrode base is associated with a conductive element for electrically connecting the base to the neuroprosthetic stimulator unit.

According to still further features in the described preferred embodiments, the conductive element is a first conductive complementary mechanical fastener, and wherein associated with the frame is a second conductive complementary mechanical fastener, the first conductive fastener being complementary to the second conductive fastener.

According to still further features in the described preferred embodiments, the electrode base is loosely associated with the first conductive fastener by means of a flexible wire, thereby enabling the electrical stimulation electrode assembly to be adjustably and reversibly positioned on the frame in a plurality of positions, according to individual needs of the user.

According to still further features in the described preferred embodiments, the electrode base is associated with the first conductive fastener by means of a flexible wire, thereby substantially decoupling an electrical connection of the electrode assembly to the stimulator unit from a mechanical connection of the electrode assembly to the stimulator unit, so as to enable the electrode assembly to be adjustably and reversibly positioned on the frame in a plurality of positions, according to individual needs of the user.

According to still further features in the described preferred embodiments, the first and second fasteners include hook and loop fasteners.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 9A is a perspective view of another embodiment of the inventive electrode assembly;

FIG. 13A is a schematic perspective view of the electrode assembly and detachable layer, according to another embodiment of the present invention;

FIG. 13B is a detailed magnification of FIG. 13A, and

FIG. 13C is a detailed, magnified, cross-sectional view of a snap connector of the electrode assembly mechanically connected to a complementary connector on the detachable layer.

DESCRIPTION OF THE PREFERRED EMBODIMENTS

Figure 1:
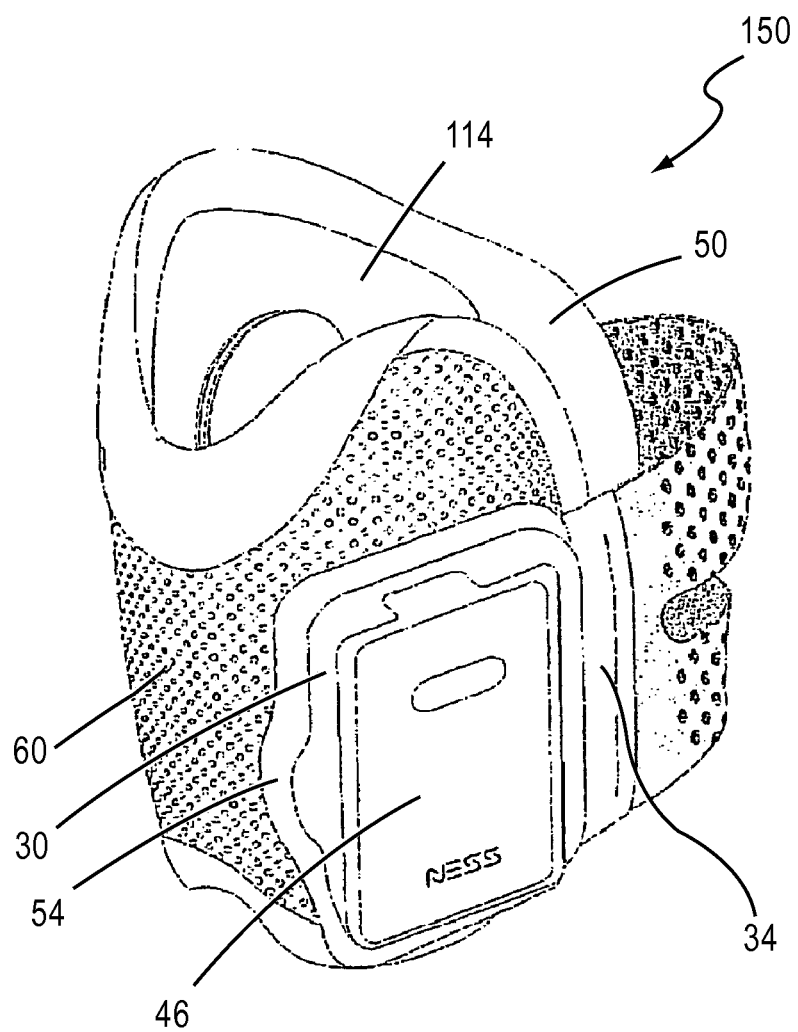
FIG. 1 is a perspective view of the inventive FES orthosis for gait modulation.

The present invention is an improved functional electrical stimulation (FES) orthosis and method, and more particularly, an FES orthosis for users suffering from gait problems such as drop foot. The orthosis can easily be donned on the leg, even by patients suffering from an impaired hand.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Figure 2:
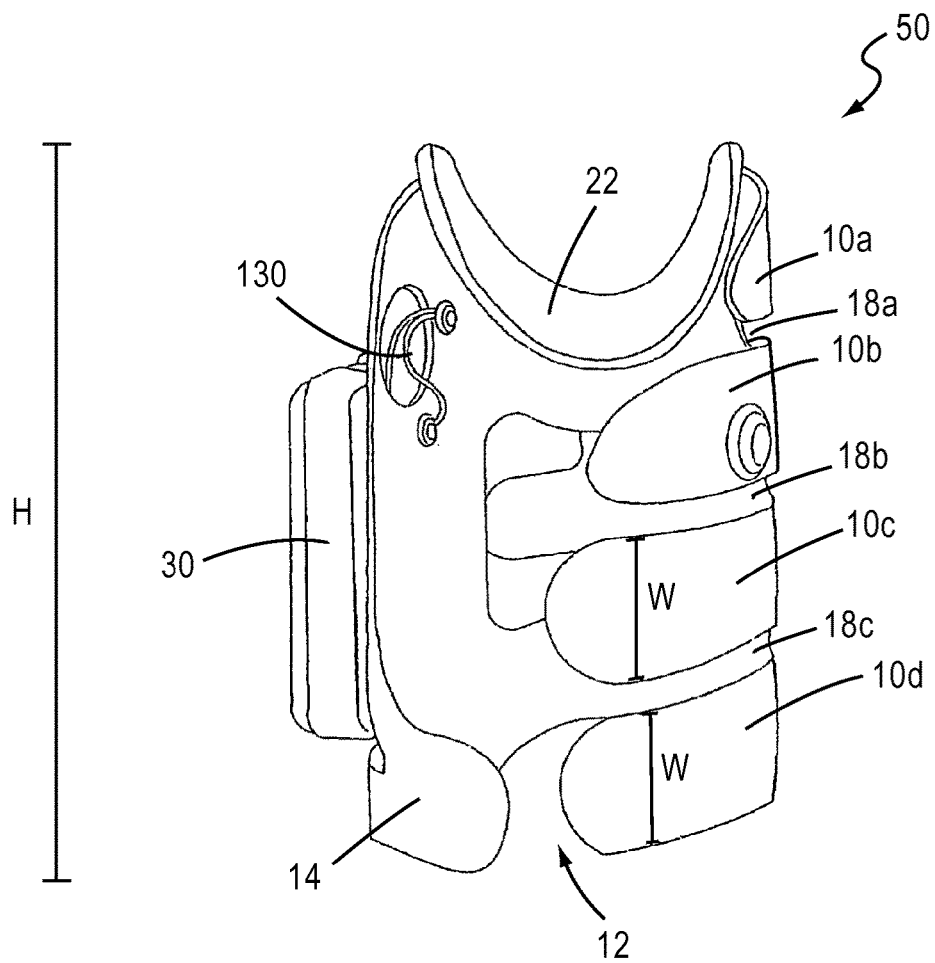
FIG. 2 is a perspective front view of a central, semi-rigid frame of the inventive FES orthosis of FIG. 1.
Figure 3:
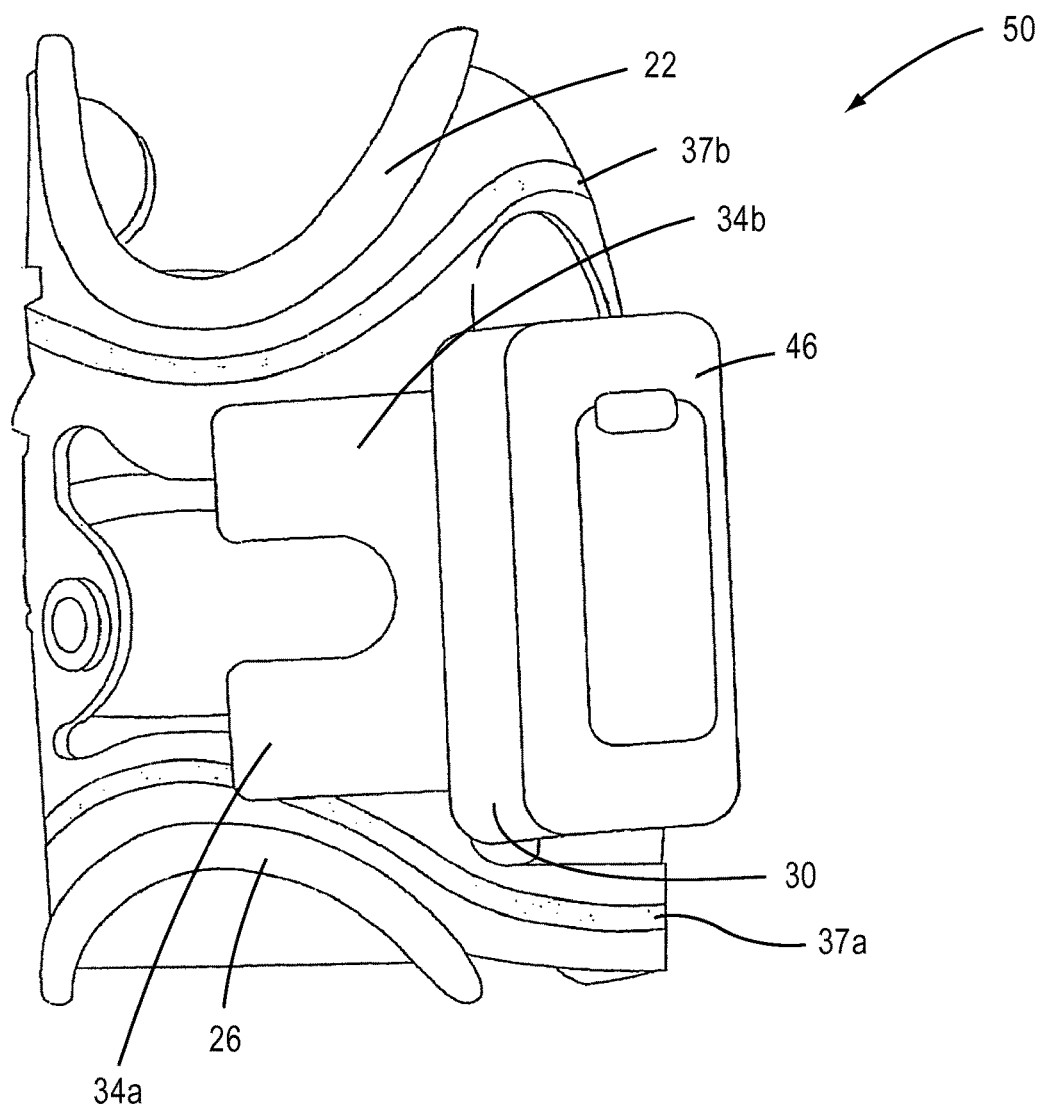
FIG. 3 is a perspective back view of the frame of FIG. 2, showing also an attached stimulator unit and housing.

Referring now to the drawings, FIG. 1 is a perspective view of the inventive FES gait modulation orthosis 150; FIG. 2 and FIG. 3 are perspective front and back views, respectively, of the central, semi-rigid frame 50 of the FES orthosis. It can be seen from these drawings that FES orthosis 150 includes three layers: central frame 50, which is at least semi-rigid, an internal soft layer 114 covering the inner facing of frame 50, and an external soft layer 60 covering the outer facing of frame 50. Additionally, orthosis 150 includes a neuroprosthetic stimulation unit 46, as well as stimulation electrode assemblies (shown in detail in FIG. 9 and described hereinbelow).

As used herein in the specification and in the claims section that follows, the term "limb segment" refers to a limb segment including a portion of the upper or lower arm, or the upper or lower leg.

As used herein in the specification and in the claims section that follows, the term "envelop", "enveloping", and the like, with regard to a limb segment and an article therefor, refers to an article that substantially surrounds and covers at least one half the circumference of a limb segment.

As used herein in the specification and in the claims section that follows, the term "reversible", "reversibly", and the like, with respect to attachment and/or detachment of an element or assembly, refers to a non-destructive, repeatable attachment and/or detachment. The term "reversible attachment", "reversibly attached", and the like, with respect to a soft layer associated with the frame of the orthosis, further refers to a reproducible positioning of the soft layer, with respect to the frame, each time the soft layer is reattached.

As used herein in the specification and in the claims section that follows, the term "inner face" refers to at least one of: the face of the detachable layer for contacting the surface of the limb segment of the user, and the face of the soft inner layer disposed within the central frame. Thus, in an orthosis in which there is no detachable layer, the term "inner face" refers to the face of the soft inner layer disposed within the central frame.

Central frame 50 is ergonomically configured to at least partially envelop the limb segment, more preferably, to surround at least ⅔ of the circumference of the limb segment, and most preferably, to substantially envelop the limb segment completely. As shown in FIG. 2, frame 50 includes at least one circumferentially retaining element pair 12 for tightly enveloping the limb. Retaining element pair 12 includes opposing, flexible and elongated members, such as flexible, elongated member 14 and flexible, elongated member 10c. Preferably, retaining element pair 12 includes flexible and elongated members that are substantially directly opposite, such as member 14 and member 10d.

In addition, flexible, elongated members 14, 10a-d are flexible, and spring-loaded towards the limb segment. Hence, in increasing the diameter of central frame 50, the pressure applied from within frame 50 must overcome the resistance of the spring-loaded retaining element pair 12, as well as the resistance of additional flexible and elongated members 10a-10c. Consequently, when orthosis 150 is donned by expanding frame 50 around the limb segment, orthosis 150 is tightly held in the desired position by retaining element pair 12 and additional members 10a-10c.

Preferably, spring-loaded metal strips 37a, 37b are disposed around the circumference of frame 50, to augment the spring-loading action of flexible, elongated members 14, 10a-d, and to maintain the efficacy of the spring-loading action over the lifetime of orthosis 150.

Central frame 50 is preferably configured to have one individual elongated member 14 on a first side of retaining element pair 12, and two to four individual elongated members 10a to 10d on the opposing side, more preferably, three elongated members, and most preferably, at least four, as shown in FIGS. 2 and 3. In this case, frame 50 resembles an open hand where individual retaining members 10a to 10d resemble fingers, and individual retaining member 14 resembles a thumb.

While inventive FES orthosis 150 can be designed to have two or more individual retaining member on each side, the inventors have found that having a single, narrow retaining member (such as retaining member 14) on one of the sides facilitates both the donning process and the doffing process. Preferably, each single, narrow retaining member 14, 10a-d has a width of 1.0-6 cm, more preferably, 2-4.5 cm, and most preferably, 2.5-3.5 cm. Within these width ranges, this single, narrow retaining member is wide enough to grip the limb segment, and narrow enough to enable facile donning of the orthotic device. With respect to the height of the orthotic device, the single, narrow retaining member has a width W within a range of 8-60% of the height of the orthotic device, more preferably, 10-35%, and most preferably, 15-30%. Above these ranges, central frame 50 acts in a more rigid fashion during the donning process and the doffing process.

Disposed between retaining members 10a to 10d are gaps 18a to 18c, as shown in FIG. 2. Gaps 18a to 18c enable elongated members 10a-10d to conform in substantially independent fashion to the contours of the limb segment, both when the limb segment is static and dynamic. It should be emphasized that various limb segments exhibit large profile changes, especially during articulations of the neighboring joints, along with activation of the muscles of the particular limb segment.

Thus, the above-described arrangement enables a superior enveloping of the limb segment by frame 50, and serves to effectively disperse the pressure and strains on the limb tissue, retaining thereby the natural profile and geometry of the limb tissue and muscles. The dispersion of pressures via flexible members 10a to 10d also enables an orthosis 150 of a particular diameter and contour to accommodate a wide variety of limb diameters and profiles.

Significantly, the open-hand shape of central semi-rigid frame 50 also allows the limb to be firmly gripped and retained in exact position by FES orthosis 150 during donning of the device, until final locking of orthosis 150, which will be described hereinbelow.

When FES orthosis 150 is donned on a leg, the above-described arrangement is particularly suitable for enabling the orthosis to adapt to anatomical changes with time, as well as to changes due to the contraction and expansion of the muscles during walking, while maintaining the stimulation electrode in accurate position against the contact points on the leg segment, and with even pressure.

Figure 3A:
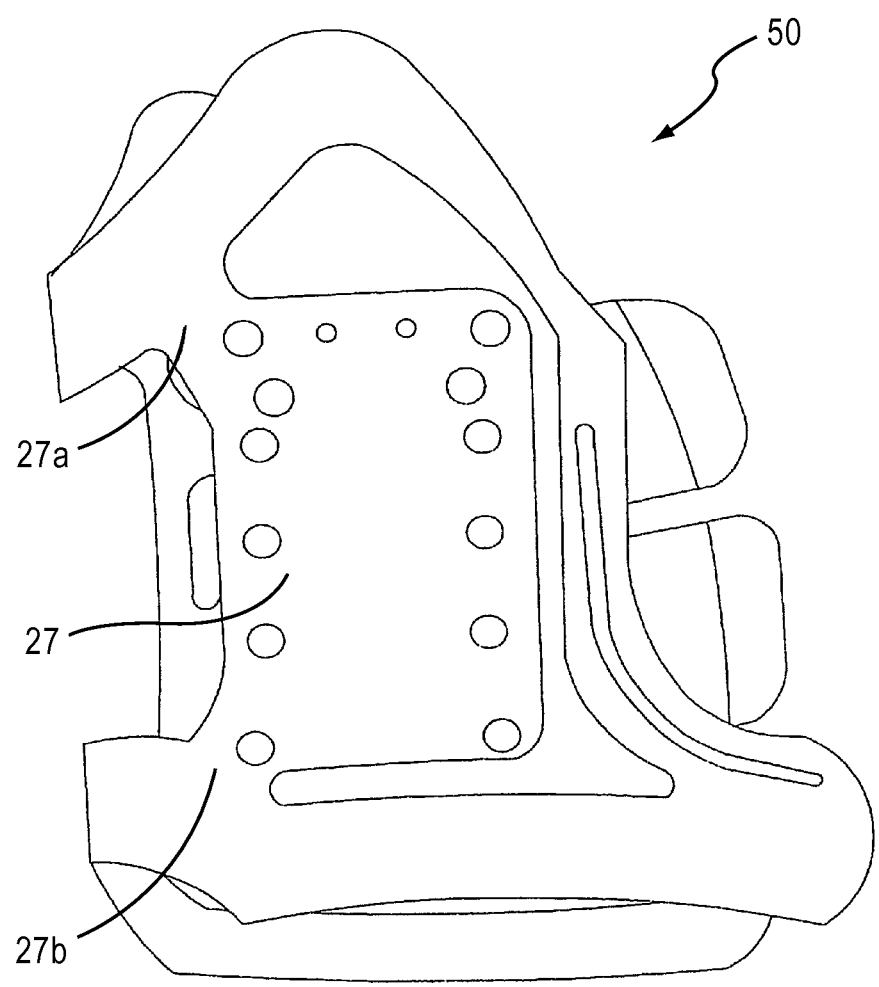
FIG. 3A is a perspective side view of the frame of the FES orthosis of FIG. 2, with the stimulator unit and housing removed to reveal a flexible leaf, integral to the frame, for supporting the stimulator unit housing.

FIG. 3A is a perspective side view of central frame 50, revealing a flexible leaf or plate 27, integral to frame 50, for supporting the stimulator unit housing or cradle 30 (not shown). Flexible leaf 27 is preferably attached to frame 50 solely on one side (or on a portion of one side), such that pressure exerted on stimulation unit 46 (not shown) is substantially absorbed solely by flexible leaf 27. This enables the surface electrical stimulation electrodes to maintain a fixed position, and with substantially even pressure, against a pre-determined position on the surface of the limb segment, even when stimulation unit 46 is knocked, pushed, or pulled. In FIG. 3A, flexible leaf 27 is connected to frame 50 solely by two narrow necks 27a, b, so as to minimize pressures and strains on frame 50 due to stimulation unit 46.

When suitably positioned below the knee, (see also FIGS. 5 and 6), orthosis 150 provides electrical stimulation to the contact points overlying the peroneal nerve and the tibialis anterior muscle, so as to modulate the gait. To guide the positioning, central frame 50 preferably includes an upper locator 22, and a lower locator 26. Upper locator 22 preferably has the form of a three-dimensional inverted arch, contoured, so as to conform to the inferior border of the tuberosity of the patella and to the characteristic anatomical recesses on each side thereof. The edge of the device is made of elastomeric material to provide comfort when positioned on the limb, and to improve the stability of FES orthosis 150 on the limb segment.

Upper locator 22 includes a molding extending from semi-rigid frame 50 so as to abut the inferior border of the patella, while lower locator 26 is designed to conform to the characteristic anatomical shape of the inferior surface of the tibial crest. When donning FES orthosis 150 on the leg, locator 22 assists both in the accurate longitudinal placement of orthosis 150 along the long axis of the lower leg segment, and in the rotational orientation about the long axis of the leg segment, as will be described in greater detail hereinbelow. Locator 26 assists in the rotational orientation about the long axis of the leg segment.

After exact positioning of FES orthosis 150 on the stimulation points has been achieved, orthosis 150 is firmly secured and locked on to the limb segment by a robust fastening arrangement 34 (shown in FIGS. 1 and 3), which is firmly associated at a first end, with central frame 50, and ends in a handle 54 at the opposite end. Fastening arrangement 34 further includes substantially parallel, elastic modular straps 34a and 34b, connecting between the first end and handle 54. Elastic modular straps 34a and 34b are designed such that during donning, straps 34a and 34b wrap circumferentially around the limb segment, to tightly lock FES orthosis 150 in place around the segment. The locking may be effected by fastening handle 54 to stimulator unit housing or cradle 30. Various exemplary alternatives for this fastening are provided hereinbelow.

Each of elastic straps 34a and 34b is equipped with an adjustment buckle 38 (see FIG. 5), so as to allow different degrees of tightening according to the contour of the leg segment and according to the needs of individual patients.

Figure 4:
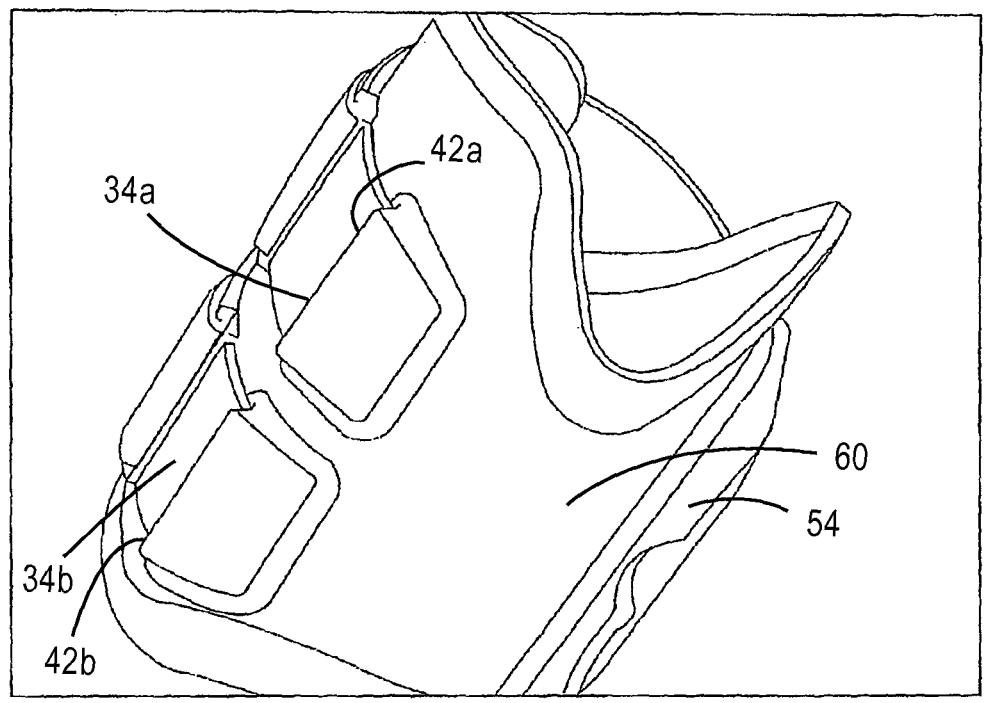
FIG. 4 is a perspective view showing a tightening mechanism of the inventive FES orthosis.

As previously mentioned, central frame 50 is covered by an external layer 60, which is made of a soft, preferably aesthetic material. Elastic straps 34a and 34b emerge through openings 42a and 42b in external layer 60, as shown in FIG. 4. This configuration eliminates or greatly reduces the distortion of central frame 50 during the securing of orthosis 150 to the leg.

Handle 54 is preferably made of an elastomeric material that imparts a flexible nature to handle 54. Preferably, handle 54 has a generally loop-like shape (hollow, with a rectangular or oval perimeter), so as to fit around stimulator cradle 30, or around any other connecting point or protuberance extending from frame 50, thereby securely locking orthosis 150 in place over the limb segment. Once positioned around stimulator cradle 30, handle 54 helps to protect stimulation unit 46 around the sides thereof, thereby providing stimulator cradle 30 and stimulation unit 46 with a smooth and unobtrusive profile. This is particularly important because knocks and pressures delivered to the surfaces of stimulation units of the prior art, in addition to being unpleasant for the user, can compromise the substantially even pressure applied by the surface electrode to the surface of the limb segment. The streamlined profile also facilitates rolling a pant leg past orthosis 150.

Fastening arrangement 34 is modular, can be easily detached from orthosis 150, and can be manufactured in several sizes.

Figure 5:
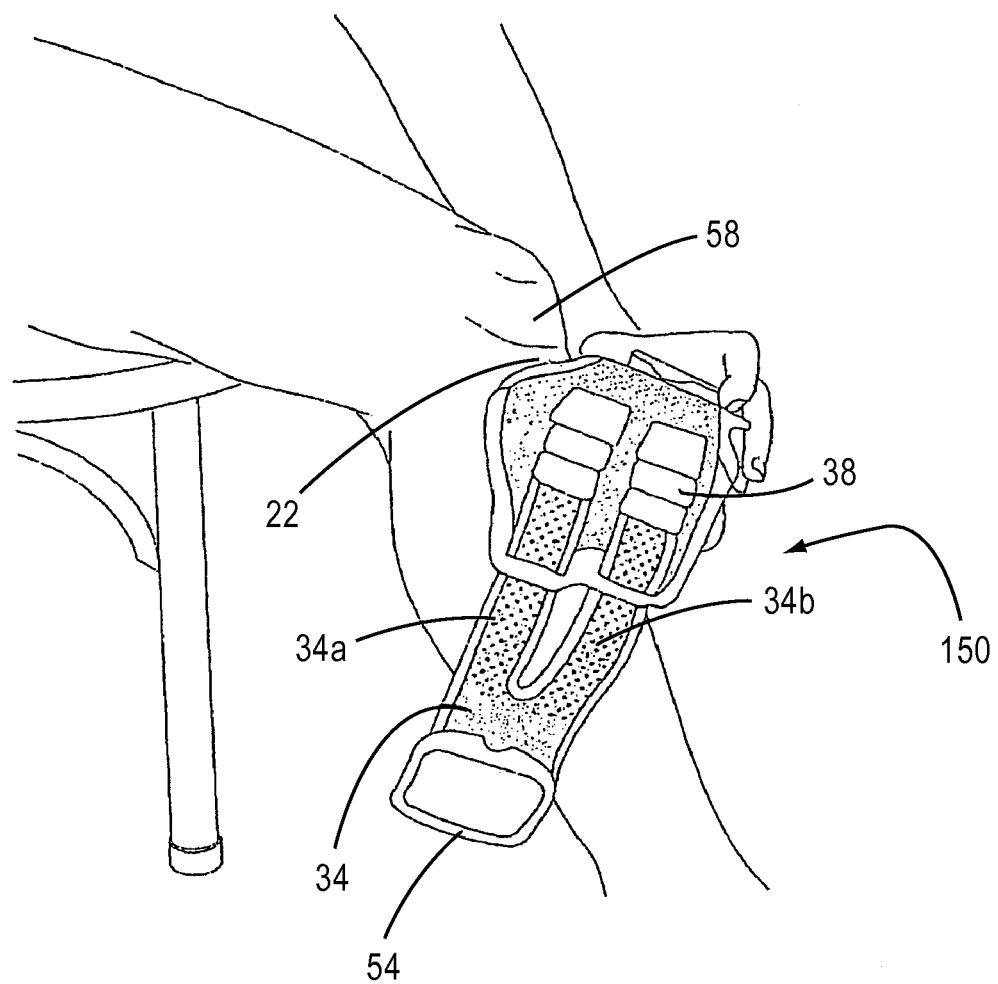
FIG. 5 illustrates a side view of the donning of the device of FIG. 1 on an impaired leg.
Figure 6:
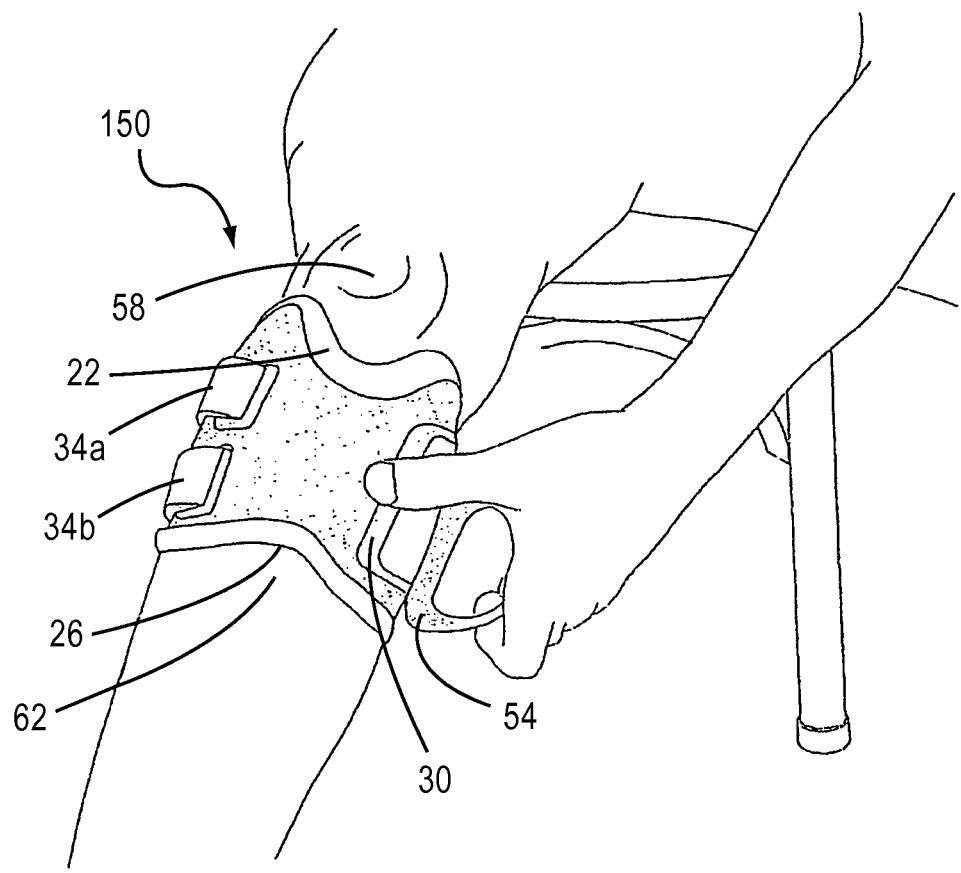
FIG. 6 illustrates a front view of the donning of the device of FIG. 1 on the impaired leg.

FIGS. 5 and 6 illustrate the donning—and subsequent locking—of FES orthosis 150 on an impaired leg. For positioning orthosis 150, while seated, it is preferable for the user to partially extend the lower leg, as shown in FIG. 5, such that the protuberance of the patella 58 is clearly defined. Subsequently, orthosis 150 is placed on the leg, such that upper locator 22 is juxtaposed against the lower facing of patella 58. Lower locator 26 should then be centered around tibial crest 62. Orthosis 150 grips the leg gently, but firmly enough to keep orthosis 150 in place, even if the user releases his grip as in the case, inter alias of hemiplegic users. Subsequently, the securing of orthosis 150 is completed by fastening arrangement 34.

An alternative donning procedure is to place FES orthosis 150 along the tibial crest 62, a few centimeters below patella 58, and then to gently slide orthosis 150 up the calf until upper locator 22 abuts against patella 58. After orthosis 150 grips the leg segment so as to retain the desired position, locking is achieved by grasping handle 54 with the fingers of the opposite hand from the leg with orthosis 150. The thumb is placed on cradle 30, to hold orthosis 150 in place, and preventing sliding down or rotation, while the hand is closed so that the loop of handle 54 fits snugly around cradle 30. Alternatively, four fingers of the hand opposite to the leg with orthosis 150 are slipped through handle 54, grasping the handle close to cradle 30. The fingers then curl onto the attachment point of cradle 30 and lever handle 54 into place while allowing handle 54 to slip off the fingers. Once handle 54 is locked in place around cradle 30, the tension of fastening arrangement 34 firmly holds orthosis 150 around the limb segment of the user, even during aggressive movement of the limb.

FES orthosis 150 is doffed by releasing handle 54 from cradle 30 and pulling orthosis 150 away from the leg segment. It should be emphasized that both donning and doffing may easily be performed, unassisted and using a single hand, by hemiplegic patients.

Members 10a to 10d and member 14 of central frame 50 are preferably made of a polymeric material that provides flexibility and spring-like characteristics to orthosis 150. This combination of structure and materials provide the following features to orthosis 150:

1. Facile placement on the leg using a single hand.
2. Spring-loaded retention or gripping of orthosis 150 in proper position prior to and during locking orthosis 150 in position. Both the facile placement of the orthosis and the self-retaining grip of the orthosis on the leg enable patients suffering from an impaired hand to effectively don the device.
3. Accurate locating and relocating of the stimulating electrode assemblies.
4. After locking of orthosis 150 on the limb, the structure and materials of these members prevent random movement and migration of orthosis 150, even during limb extensions, flexions and gait.
5. Uniform dispersion of the pressure and strains to the limb tissue, thus retaining the natural profile and geometry of the limb tissue and muscle.
6. Uniform pressure of the electrodes against the surface of the limb segment.

Figure 7:
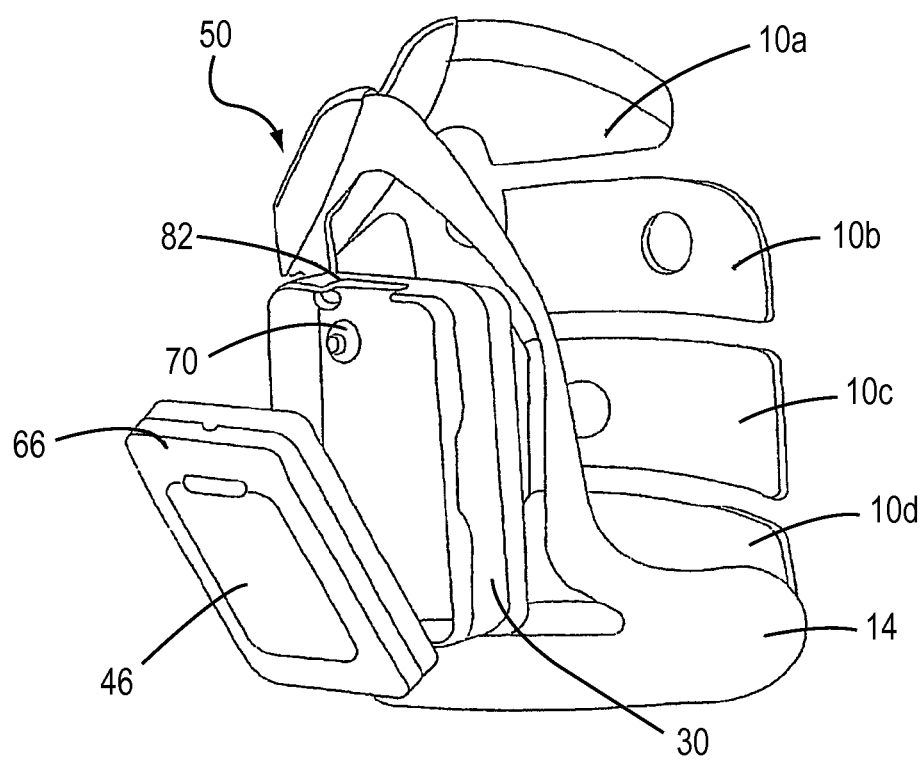
FIG. 7 is a perspective view showing the attachment of a neuroprosthetic stimulator unit to the FES orthosis of FIG. 1.

Referring now to FIGS. 1, 3 and 7, stimulator unit 46 is associated with orthosis 150 by means of cradle 30, which is a receptacle integrated onto the external surface of central frame 50.

Cradle 30 is advantageously designed to have concave edges for receiving a thumb during the donning procedure. Placing the thumb on the edges of cradle 30 enables the formation of a counter-force for urging handle 54 towards cradle 30. The backside of cradle 30 has a concavity similar to that of central frame 50, such that the overall contour can adapt to the contour of the limb segment.

Stimulator unit 46 is small and has a thin profile, so as to minimally protrude from the surface of orthosis 150, and is lightweight, to avoid superfluous weight on the impaired leg.

Figure 8:
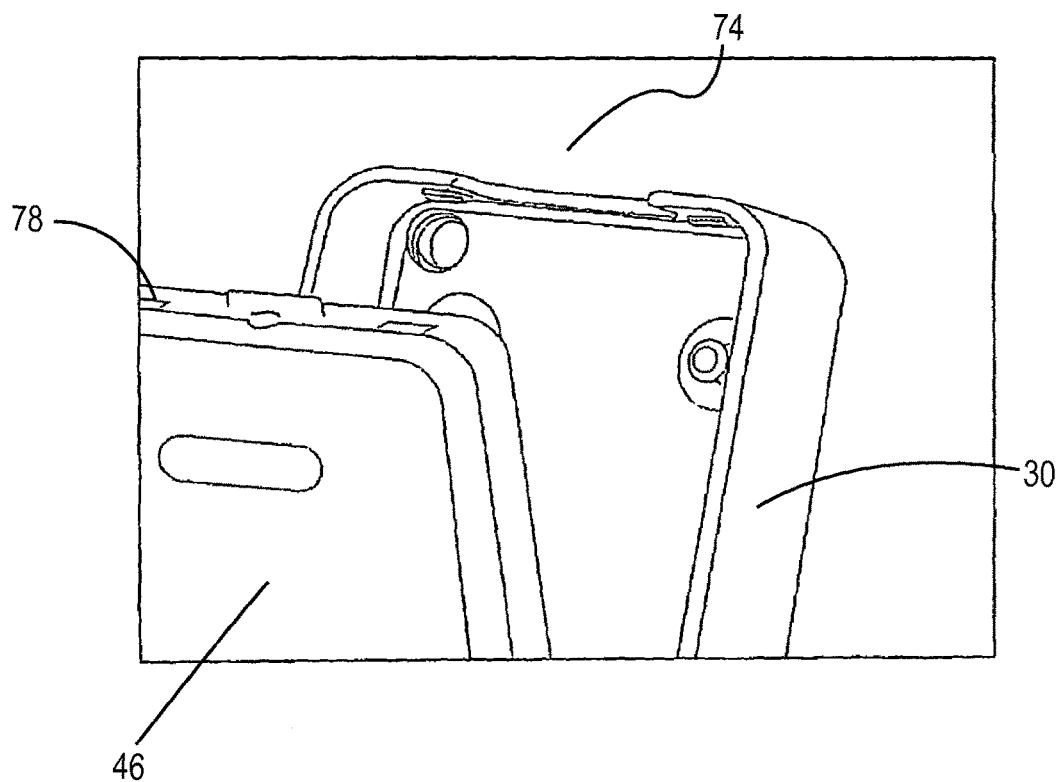
FIG. 8 illustrates the association of the neuroprosthetic stimulator unit with a cradle of the FES orthosis of FIG. 1.

Stimulator unit 46, as shown in FIGS. 7 and 8, is electrically connected to cradle 30 by connectors 66 and 70 disposed on stimulator unit 46 and on cradle 30, respectively. In one preferred embodiment, these connectors are complementary connectors. As shown, connector 66 is a complementary female snap, and connector 70 is a corresponding male snap. Stimulator unit 46 is mechanically connected to cradle 30 by complementary mechanical connectors 74 and 78. In the embodiment shown in FIG. 8, these connectors are male latch 74 disposed on an edge of cradle 30, and a female latch receiver 78 disposed on an edge of stimulator unit 46. An additional notch 82 in cradle 30 allows pulling stimulator unit 46 with a finger or thumb to release it from cradle 30. These connective features enable facile detaching and reattaching of stimulator unit 46 from, or to, cradle 30 using a single hand.

Figure 9:
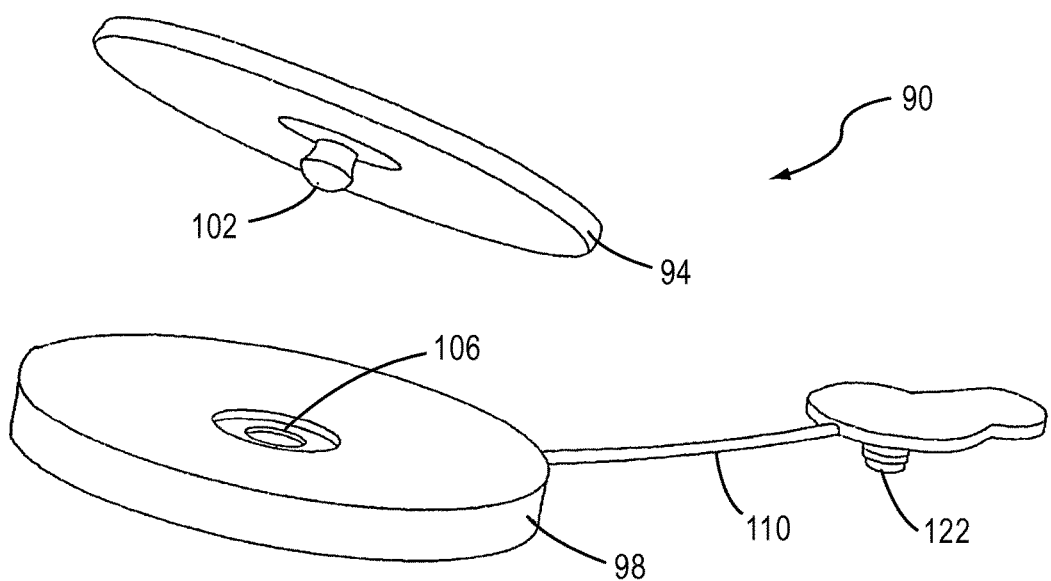
FIG. 9 is a perspective view of an electrode assembly of the inventive FES orthosis of FIG. 1.
Figure 9B:
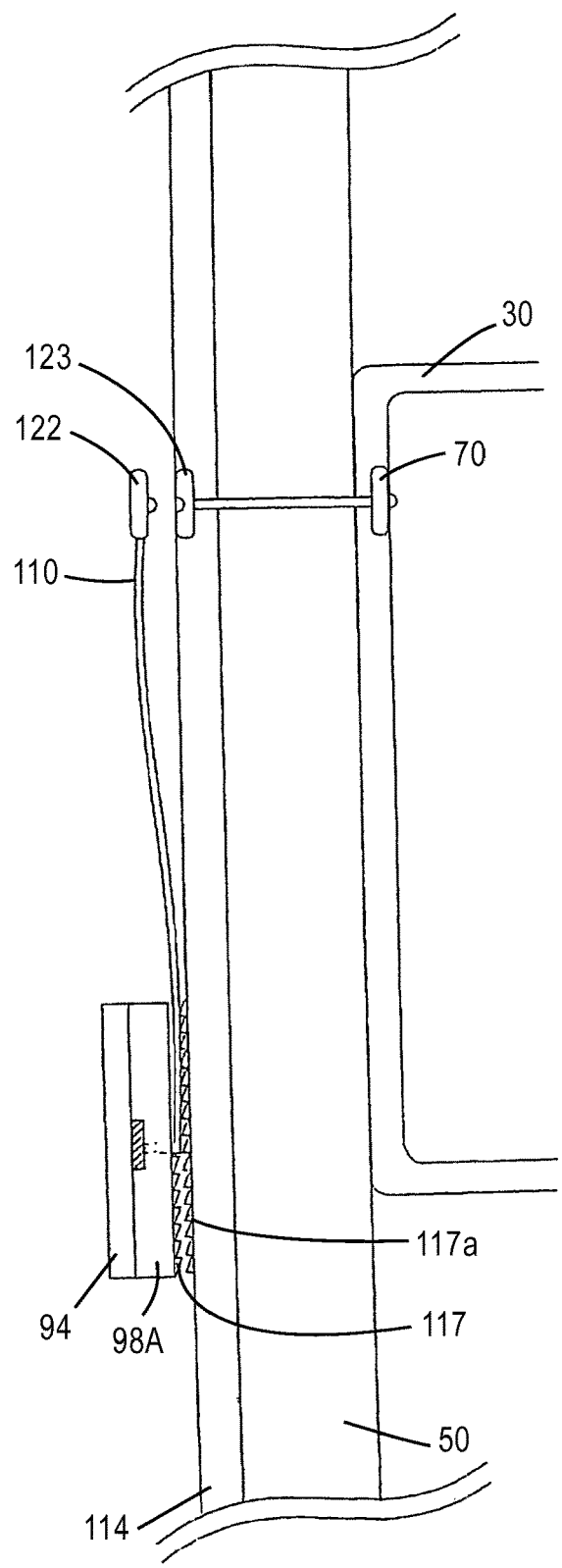
FIG. 9B is a schematic side view of a portion of the inventive FES orthosis, showing electrical and mechanical connections between the layers of the orthosis.
Figure 10:
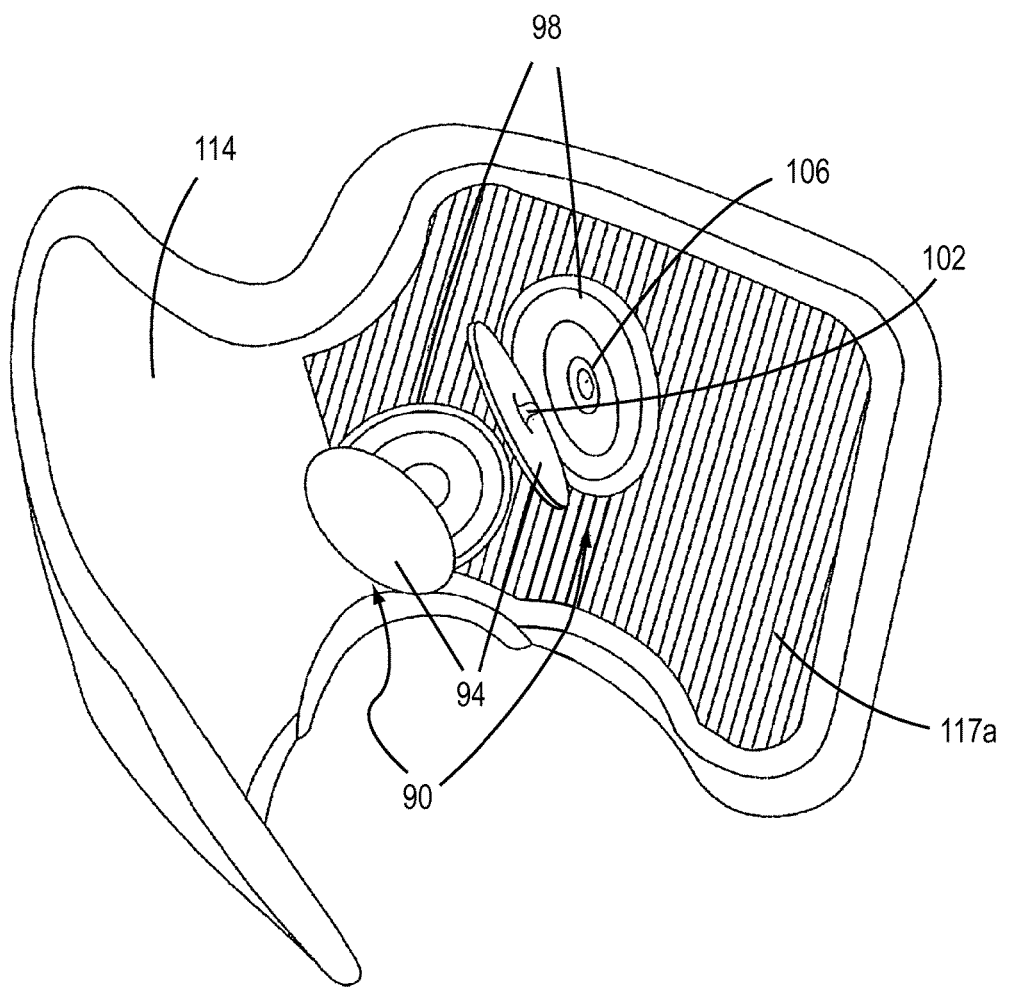
FIG. 10 is a perspective view of two electrode assemblies of FIG. 9 attached to an internal soft layer of the device of FIG. 1.

Referring now to FIG. 9, FIG. 9B and FIG. 10, FIG. 9 is a perspective view of an electrode assembly 90 of inventive orthosis 150 (not shown). Electrode assembly 90 includes a surface electrode 94, an electrode base 98, and complementary conductive connectors 102 and 106. Electrode assembly 90 further includes a conductive wire 110, which, at a first end, is mechanically connected to electrode base 98 so as to provide an electrical connection to connector 106. Conductive wire 110 terminates at a second end with a complementary conductive connector 122, which mechanically connects electrode assembly 90 to central frame 50 (as shown below in FIG. 9B), and electrically connects electrode assembly 90, via central frame 50, to stimulator housing 30 (also shown below in FIG. 9B).

In the exemplary embodiment shown in FIG. 9, complementary connector 102 is a male snap connector associated with surface electrode 94, while complementary connector 106 is a female snap connector connected to electrode base 98. Both surface electrode 94 and electrode base 98 are made of flexible materials that enable them to conform to the limb tissues.

Electrode base 98 is preferably concave-shaped, such that the connection between complementary connector 102 of surface electrode 94 and complementary connector 106 of electrode base 98 is recessed within a recess, thereby preventing excessive local pressure of the snaps 102 and 106 on the underlying skin. The concave, 3-dimensional shape of the top surface of electrode base 98 also provides a substantially even contact pressure of surface electrode 94 to the skin.

Surface electrode 94 preferably has a large surface area, with respect to many FES leg devices of the prior art, which serves to assuage discomfort from the electrical stimulation. The surface area of surface electrode 94 is preferably at least about 9 cm$^2$, more preferably at least about 12 cm$^2$, and even more preferably, at least about 15 cm$^2$. In some cases, the surface area of surface electrode 94 is as much as about 20 cm$^2$. It is presently preferred that the surface area of surface electrode 94 is within a range of 12-20 cm$^2$. By sharp contrast, the surface area of each surface electrode of the prior art devices such as the WalkAide™ device is less than 5 cm$^2$.

In contrast to prior art FES leg devices, the electrode separation in the FES orthosis of the present invention is preferably as large as anatomical constraints permit, particularly in the direction along the length of the limb. The distance between electrode centers is at least about 5 cm and the longitudinal separation is at least about 3 cm, and preferably at least 3.5 cm.

FIG. 9A is a perspective view of another embodiment of an electrode assembly 90A of inventive orthosis 150 (not shown). Electrode assembly 90A includes a surface electrode 94A, an electrode base 98A, and a wire 110, which terminates with complementary connector 122. In the exemplary embodiment shown in FIG. 9A, surface electrode 94A has first and second faces 95, 97 made of hydrogel or any another conductive, adhesive material known in the art for use in surface electrodes. First face 95 is for flexibly adhering to the skin of the user, while the opposite second face 97 is for adhering to a top face 99 of electrode base 98A. On top face 99 is disposed a conductive region 106A, for electrically connecting with second face 97. Preferably, top face 99 of electrode base 98A is also provided with a rim 101 for tightly receiving surface electrode 94A, such that the relative position of electrode 94A and electrode base 98A is uniquely defined and determined. The connection of electrode 94A and electrode base 98A may be further enhanced by disposing, on top face 99 of electrode base 98A, patches 103 of hook fasteners (e.g., plastic Velcro® hooks), which surprisingly hold on to the substantially flat, hydrogel surface of second face 97.

Substantially as described above with respect to FIG. 9, conductive wire 110 is mechanically connected to electrode base 98 so as to provide an electrical connection to conductive region 106A.

The relationship between electrode assembly 90 and internal soft layer 114, shown in FIG. 10, is also relevant for the alternative embodiment presented in FIG. 9A and described hereinabove. Electrode base 98 is attached to internal layer 114 by complementary connectors 117 and 117a, preferably hook and loop fasteners such as Velcro®, which are best seen in FIG. 9b.

The electrical connections are made as follows: complementary connector 122 connects to a complementary connector 123, which is disposed in a fixed position on internal layer 114 or on central frame 50. Electrical stimulation is achieved by directing a current from stimulator unit 46 (not shown), via connector 70 disposed on housing 30, through frame 50 and internal layer 114, to connector 123, and ultimately, to electrode assembly 90A and stimulator housing 30 with connector 123.

In the exemplary embodiments shown, complementary connector 122 is a conductive male snap connector, and complementary connector 123 is a conductive female snap connector.

It will be appreciated that the design of electrode base 98 and the design of connectors 122 and 123 enable a wide range of positioning of each electrode assembly 90. Unlike various prior art devices, the position of electrode 94 is not limited to a position in which electrode 94 physically touches a conductive element fixed in the body of the orthosis (such as connector 123). Rather, the position of electrode 94 is substantially decoupled with respect to such fixed conductive elements. Wire 110 should be long enough to enable the full range of positioning.

In addition, the above-described design enables the clinician to exactly define the position of each electrode assembly 90 in a first step, and then, in a second step, to attach the assembly to FES orthosis 150 by means of complementary connectors 122 and 123. Thus, during the initial setup procedure, the clinician needs to position solely the surface electrodes or electrode assemblies (e.g., electrode assembly 90A)—and not the entire orthosis 150—on the stimulation points of the muscles to be activated. In order to define the exact position, the clinician activates the electrodes, which can electrically be connected directly to stimulator unit 46. Subsequently, the clinician connects each surface electrode 94 to the respective electrode base 98 prior to donning orthosis 150 on the leg and prior to attaching each electrode base 98 to internal layer 114 or to central frame 50. Once orthosis 150 has been donned, each electrode base 98 attaches, by means of complementary connectors 117 and 117a (shown in FIG. 9B), to internal layer 114 of orthosis 150.

Stimulation by means of the two electrode assemblies 90, illustrated in FIG. 10, produces dorsi-flexion of the foot. To ensure electrical contact between surface electrode 94 and the skin surface, surface electrode 94 may be smeared by conductive gel or hydrogel or covered by a cloth pad that has been soaked in a conductive liquid such as water. The face of surface electrode 94 for contacting the skin may advantageously be a flexible hydrogel layer.

Electrode assemblies 90 conform to the three-dimensional shape of the underlying limb, and adapt their shape during limb articulations and muscle contractions. Electrode base 98 and surface electrode 94, which are essentially elastic, lie pressed between internal soft layer 114 and the skin surface, such that a minimal resistance is supplied to the changing limb geometry.

Figure 11:
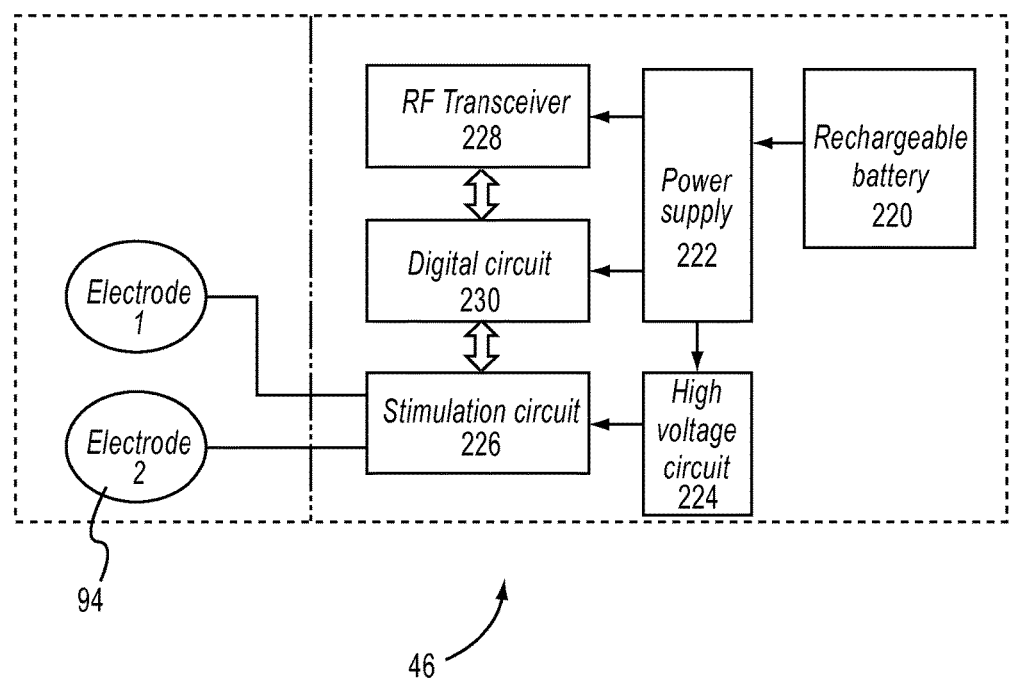
FIG. 11 is a block diagram showing the main features of the electrical stimulation unit.

Referring now to FIG. 11, stimulator unit 46 is electrically connected with at least one stimulation electrode, such as surface electrode 94. Stimulator unit 46 is preferably powered by a rechargeable battery 220 that is electrically connected to an internal power supply 222. Power supply 222 supplies power to a high-voltage circuit 224 feeding into stimulation circuit 226. Preferably, stimulator unit 46 communicates with a stimulator control unit and/or a limb or motion sensor (described hereinbelow) by means of a radio frequency (RF) transceiver 228. Power supply 222 supplies power at a lower voltage to RF transceiver 228, and to a digital circuit 230 interfacing between RF transceiver 228 and stimulation circuit 226.

As used herein in the specification and in the claims section that follows, the term "radio frequency" refers to electromagnetic waves, preferably having a frequency within the radio frequency range. The currently preferred range is 2400-2483.5 GHz.

During operation, the battery-operated control unit maintains two-way communication with stimulator unit 46.

The control unit enables to switch on the device, select the operating mode of the device (gait mode, training mode, or returning to standby mode), and adjust the intensity of stimulation and volume of an audio alert.

Additionally, each of the system components (FES orthosis 150, control unit and foot sensor) is preferably represented by graphic icons on the control unit. LEDs of different colors emit light under the relevant icon so as to indicate attention-requiring events such as low battery or a malfunction of any individual component. Other LEDs indicate stimulating or resting, stimulation intensity, or training mode.

The control unit preferably has an audio alert that produces an audio signal so as to alert the user when: the system is first switched on, a button has been pressed, a mode has been selected, the battery is low, radio communication between components of the device is lost, or, other faults requiring the attention of the user have occurred.

The control unit may be waist-mounted, hung by means of a neck strap, or mounted by an in-pocket hold.

The foot sensor unit may be any of various foot sensor units known in the art, including a force sensor disposed underneath the foot of a user, a tilt sensor, etc.

Figure 12A:
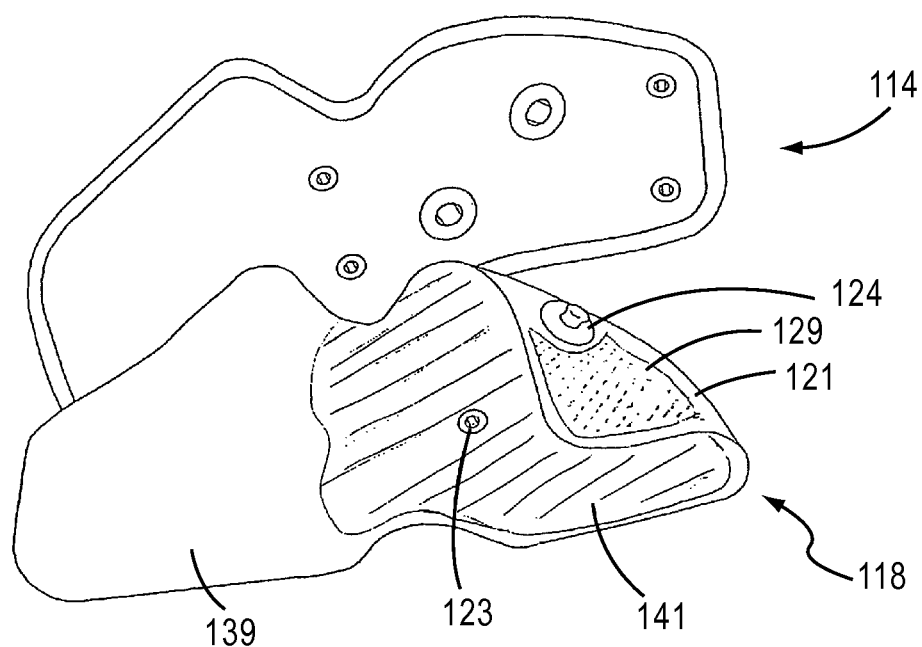
FIG. 12A is a front view of a detachable layer of the FES orthosis, according to one aspect of the present invention.
Figure 12B:
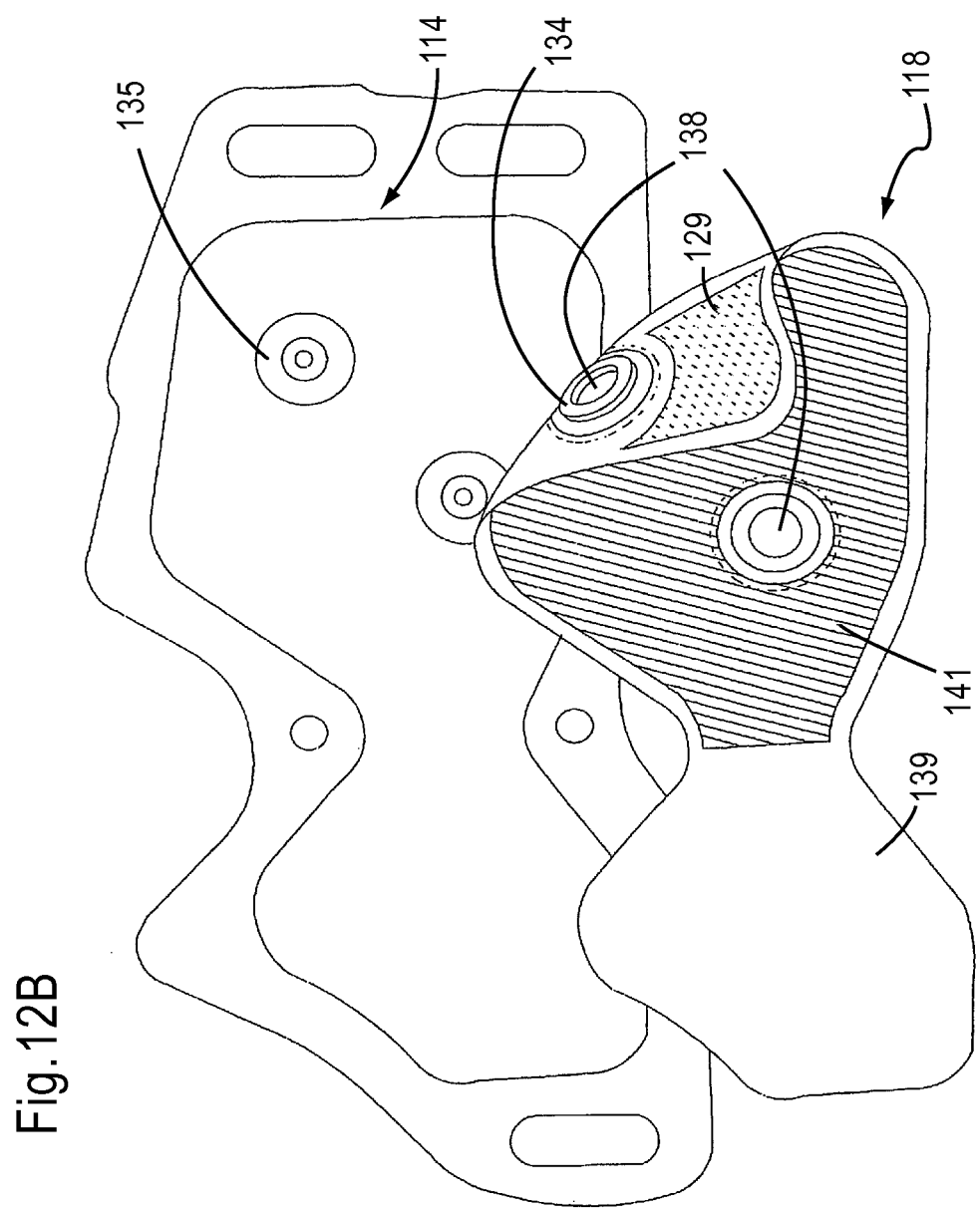
FIG. 12B illustrates another embodiment of the inventive detachable layer, having hollow snap connectors for securing the detachable layer to the internal layer of the orthosis.

FIGS. 12A-12E schematically depict another aspect of the present invention. FIGS. 12A and 12B show a front view of a personal panel or detachable layer or liner 118 for attaching to the orthosis, either to internal soft layer 114, as shown in a schematic side cross-sectional view of a slice of the orthosis in FIG. 12D, or directly to frame 50, as shown in the identical view in FIG. 12E.

Detachable layer 118 preferably has, substantially, the shape of internal soft layer 114. Detachable layer 118 is soft, so as to provide a comfortable feel on the skin surface of the user, but is provided with sufficient rigidity to maintain the alignment of each electrode assembly 90 and to make it easier to position detachable layer 118 to the orthosis. Suitable materials for detachable layer 118 include various non-woven materials such as Nordenia™ loop. Detachable layer 118 preferably has a top facing 139 having a plurality of complementary connectors 141, such as loop fasteners, disposed on the surface.

Detachable layer 118 may include the compatible electrical connectors of internal layer 114. Thus, detachable layer 118 may include male snap connectors 124 on a back surface 121 facing FES orthosis 150 and complementary connectors such as female snap connector 123 on top facing 139, for receiving complementary connector 122 (shown in FIGS. 9, 9A, and 9B) and described hereinabove. In this arrangement, detachable layer 118 is attached by the clinician to internal layer 114, or to another portion of the orthosis, such as frame 50, by means of snap connectors 124.

This provides the requisite electrical contact, and ensures accurate, singular, repeatable positioning and fixing of detachable layer 118 onto internal layer 114 and/or with respect to frame 50. Alternatively, back surface 121 has at least one patch 129 of hook or loop connectors that fix detachable layer 118 to internal layer 114. In FIG. 12A, by way of example, patch 129 includes hook connectors.

In another preferred embodiment, shown in FIG. 12B, detachable layer 118 includes holes 138, which are advantageously disposed to line up between complementary male connectors 122 of electrode assembly 90 and complementary female connectors 123 on internal layer 114, such that connector 122 connects electrode assembly 90—mechanically and electrically, to stimulator unit housing 30.

It must be emphasized that the repositioning of detachable layer 118 on FES orthosis 150, for a particular individual, restores accurate, substantially repeatable positioning of the electrode assemblies 90, even when FES orthosis 150 is a standard, universal unit that has not been adapted to the needs of that individual. Thus, in sharp contrast to prior art devices, inventive detachable layer 118 enables the clinician to use a single FES orthosis 150 for treating many users in the clinic. An individual detachable layer 118 is dedicated for a particular user. Each particular user undergoes a pre-fitting session with the clinician, so as to customize the electrode positioning for the needs of that user. Subsequently, detachable layer 118 is used repeatedly in future clinical sessions of the user. The clinician, who works with many users each day, simply removes the pre-fitted internal soft layer belonging to the previous user and attaches the pre-fitted internal soft layer belonging to the current user. The detachable layer also serves as a hygienic layer where the device is shared between users.

The replacement of the detachable layer 118, with no need to relocate the electrode assemblies 90 for each patient, enables the clinician to provide efficient, effective treatment to numerous orthosis users in a short period of time. Detachable layer 118 is preferably disposable. Alternatively, detachable layer 118 is washable.

According to another preferred embodiment of the present invention, shown schematically in FIG. 12B, a hollow snap connector 134, which is preferably an annular or oval hollow snap connector, is associated with a perimeter of hole 138 of detachable layer 118. Hollow snap connector 134 accurately and reliably snaps into a corresponding hole or recess 135, thus ensuring that detachable layer 118 is tightly attached to internal layer 114, and is exactly positioned in the same location upon each application. In addition, hollow snap connector 134 also serves for mechanically attaching complementary connector 122 of electrode assembly 90 to internal layer 114, via detachable layer 118.

Hollow snap connector 134 can be made of a plastic, flexible material such as PVC.

Figure 12C:
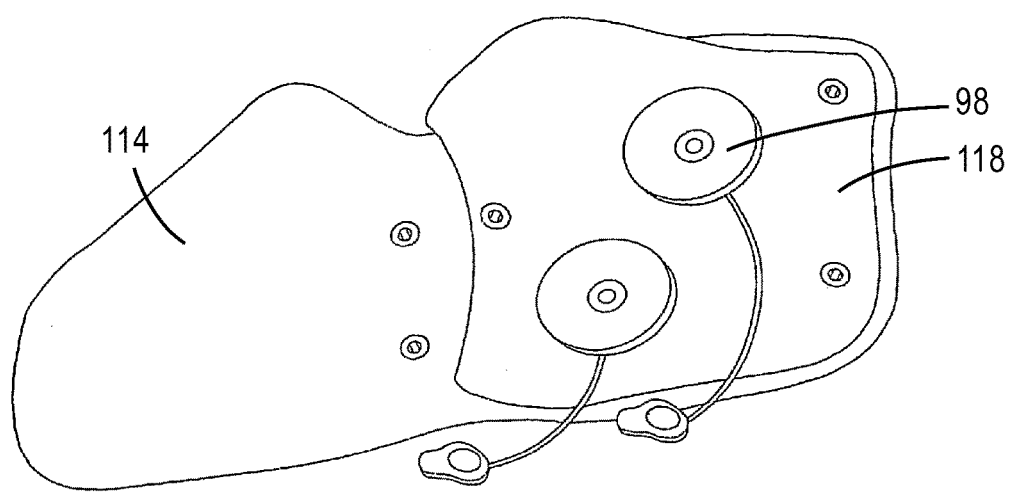
FIG. 12C illustrates another embodiment of the inventive detachable layer, in which the layer covers only a portion of the surface of the internal layer of the orthosis.

It should be appreciated that detachable layer or liner 118 may also have a shape other than the contour of internal layer 114. For example, detachable layer 118 may cover only a portion of the surface of orthosis 150, as shown in FIG. 12C. FIG. 12C also shows electrode base 98 affixed to detachable layer 118.

Figure 12D:
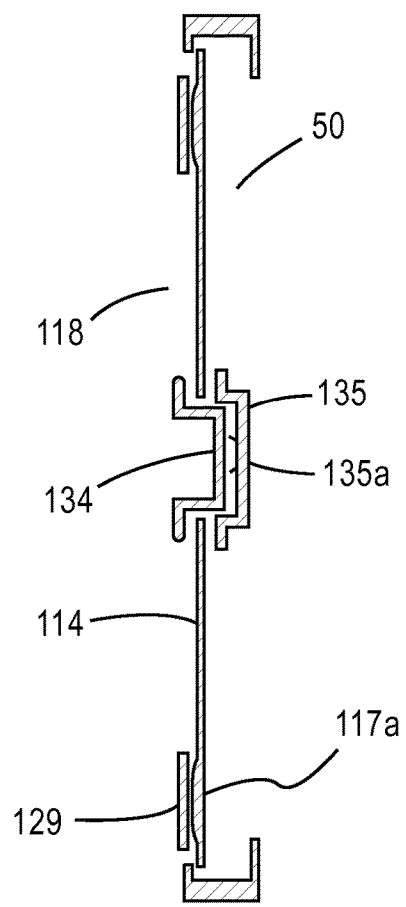
FIG. 12D is a schematic cross-sectional side view of a slice of a portion of the inventive FES orthosis, showing some of the electrical and mechanical connections between the detachable lining and other components of the orthosis.
Figure 12E:
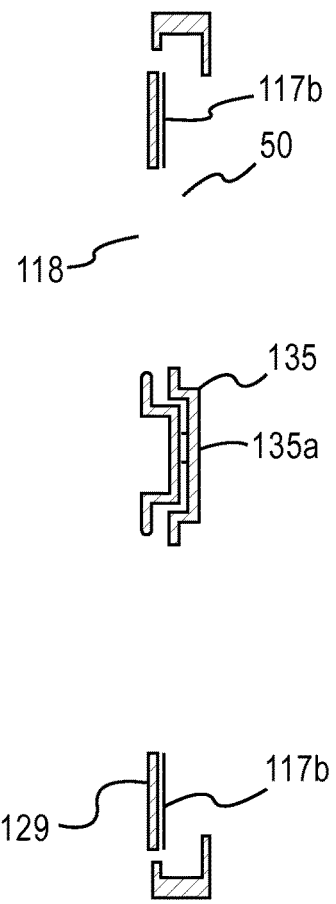
FIG. 12E is a schematic cross-sectional side view of a slice of a portion of the inventive FES orthosis, showing some of the electrical and mechanical connections between the detachable lining and other components of the orthosis, wherein the detachable lining is directly attached to the orthosis frame.

FIGS. 12D and 12E, described briefly hereinabove, show some of the main electrical and mechanical connections between detachable layer 118 and other components of the orthosis, wherein, in FIG. 12D, detachable layer 118 is attached to central frame 50 and to internal layer 114, and wherein, in FIG. 12E, layer 118 is directly attached to central frame 50.

In FIG. 12E, a complementary connector such as hollow snap connector 134, is disposed on detachable layer 118. Hollow snap connector 134 accurately and reliably snaps into a corresponding hole or recess 135 disposed in central frame 50, so as to directly connect detachable layer 118 to central frame 50. This also ensures that detachable layer 118 is tightly associated with internal layer 114, and that detachable layer 118 is exactly positioned, with respect to central frame 50, in the same location upon each application.

As described hereinabove with reference to FIG. 12A, back surface 121 of detachable layer 118 preferably has at least one area or patch 129 of complementary connectors (e.g., hook or loop connectors) that fix detachable layer 118 to internal layer 114 (via complementary connectors 117*a*).

The description of the attachments of FIG. 12D largely applies to those of FIG. 12E. In FIG. 12E, however, detachable layer 118 is juxtaposed against central frame 50, consequently, patch 129 of complementary connectors on back surface 121 is configured to fix detachable layer 118 to central flame 50 by means of complementary connectors 117*b*.

With reference to FIGS. 13A-C, and FIGS. 12D-E, FIG. 13A is a schematic perspective view of electrode assembly 90 and detachable layer 118, according to another embodiment of the present invention. As above, detachable layer 118 is equipped with hollow snap connector 134, which, as shown and described hereinabove, is configured to accurately and reliably snap into a corresponding complementary recess 135 disposed in central frame 50, so as to directly connect detachable layer 118 to central frame 50.

A complementary conductive connector 222 of electrode assembly 90 has a conductive snap 222B (shown in FIG. 13C) designed to pass through a hole such as hole 138 of hollow snap connector 134, and into a complementary area 135*a* of complementary recess 135 so as to both mechanically and electrically connect electrode assembly 90 to central frame 50. The perimeter of complementary conductive connector 222 has fins or protruding elements 222A, for snap connecting into the complementary contour of hollow snap connector 134.

Thus, hollow snap connector 134 mechanically connects to complementary recess 135, complementary conductive connector 222 mechanically connects to hollow snap connector 134 by means of protruding elements 222A, and complementary conductive connector 222 electrically connects to complementary recess 135 by means of conductive snap 222B.

It should be emphasized that complementary conductive connector 222 can be directly attached to complementary recess 135 when no personal panel is used in the orthosis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method, comprising:
    coupling, via an electrode base, a surface electrode to an inner layer of a frame, the inner layer of the frame being coupled to an inner surface of the frame;
    disposing the frame about a portion of a limb such that the frame at least partially envelops the portion of the limb, a diameter of the frame being increased during the disposing, the frame and the inner layer of the frame collectively configured such that the electrode base is disposed at a predetermined position relative to the portion of the limb when the frame and the inner layer are disposed about the portion of the limb, a retention portion of the frame configured to retain the frame about the portion of the limb, at least a portion of the retention portion being biased towards the portion of the limb after the disposing such that an inward force is imparted to the portion of the limb; and coupling, via a mounting portion of the frame, an electrical stimulator to the frame such that the stimulator is electrically coupled via a connector assembly to the electrode base, at least a portion of the connector assembly disposed within a connector opening defined by the frame.

2. The method of claim 1, wherein the predetermined position includes at least one of a longitudinal position of the electrode base relative to the limb or a rotational position of the electrode relative to the limb; the frame including a first locator disposed on a first edge portion of the frame and configured to identify the longitudinal position and the rotational position of the frame relative to the portion of the limb, the frame including a second locator, different from the first locator, disposed on a second edge portion of the frame, different from the first edge portion, the second locator configured to identify the rotational position of the frame relative to the portion of the limb.

3. The method of claim 1, wherein the predetermined position is adjacent at least one of a nerve or a muscle when the frame is disposed about the portion of the limb such that electrical stimulation transmitted to the predetermined position via the surface electrode results in flexion of a foot.

4. The method of claim 1, wherein the predetermined position overlies a motor nerve in the lower leg.

5. The method of claim 1, wherein the retention portion includes a first member and a second member, an end portion of the first member spaced apart from an end portion of the second member to define an opening, the disposing the frame about the portion of the limb includes disposing the portion of the limb through the opening, further comprising:

fastening a fastening strap across the opening after the frame is disposed about the portion of the limb.

6. The method of claim 1, further comprising:
disposing a fastening strap coupled to the frame about a portion of the frame and about a portion of the electrical stimulator.

7. The method of claim 1, further comprising:
reversibly coupling the surface electrode to the inner layer via a hook and loop fastener, at least a portion of the hook and loop fastener coupled to the electrode base.

8. The method of claim 1, further comprising:
matingly coupling a connector of the mounting portion to a complementary connector of the electrical stimulator to couple the mounting portion to the electrical stimulator.

9. The method of claim 1, further comprising:
disposing a protrusion of the mounting portion within an opening of the electrical stimulator to couple the mounting portion to the electrical stimulator.

10. The method of claim 1, wherein:
the retention portion includes a first member and a second member,
before the disposing, an end portion of the first member is spaced apart from an end portion of the second member by a first distance to define an opening,
after the disposing, the end portion of the first member is spaced apart from the end portion of the second member by a second distance to define the opening, the second distance greater than the first distance,
the disposing the frame about the portion of the limb includes disposing the portion of the limb through the opening.

11. An apparatus, comprising:
a first orthosis layer configured to at least partially envelop a portion of a limb, the first orthosis layer configured to be enlarged in circumference when the first orthosis layer at least partially envelops the portion of the limb, the first orthosis layer including a semi-rigid retention portion and a mounting portion, the retention portion configured to partially surround the portion of the limb, the retention portion configured to retain the first orthosis layer about the portion of the limb, at least a portion of the retention portion being biased towards the portion of the limb when the first orthosis layer at least partially envelops the portion of the limb, the mounting portion configured to receive at least a portion of an electrical stimulator;

a second orthosis layer coupled to an inner surface of the first orthosis layer, the second orthosis layer configured to be coupled to a surface electrode, the first orthosis layer and the second orthosis layer collectively configured such that the surface electrode is disposed at a predetermined position overlying a target stimulation point of the limb when the first orthosis layer and the second orthosis layer are disposed about the portion of the limb; and a connector assembly configured to electrically couple the electrical stimulator to the surface electrode, at least a portion of the connector assembly configured to be disposed within a connector opening defined by at least one of the first orthosis layer or the second orthosis layer.

12. The apparatus of claim 11, wherein the retention portion includes a first member and a second member, an end portion of the first member spaced apart from an end portion of the second member, the first member and the second member configured to exert a force about the portion of the limb when the first orthosis layer is disposed about the portion of the limb.

13. The apparatus of claim 11, further comprising:
a fastening strap configured to removably couple the first orthosis layer to the portion of the limb, a first portion of the fastening strap fixedly coupled to the first orthosis layer, a second portion of the fastening strap configured to be disposed about the electrical stimulator.

14. The apparatus of claim 11, wherein the second orthosis layer includes an electrode base having at least a portion of a hook and loop fastener to reversibly couple the surface electrode to the second orthosis layer.

15. The apparatus of claim 11, wherein the mounting portion includes a connector configured to be matingly coupled to a complementary connector of the electrical stimulator to couple the mounting portion to the electrical stimulator when the portion of the electrical stimulator is received by the mounting portion.

16. The apparatus of claim 11, wherein the mounting portion includes a cradle defining a recess configured to receive the electrical stimulator to couple the mounting portion to the electrical stimulator.

17. An apparatus, comprising:
a frame assembly configured to substantially envelop a portion of a limb, the frame assembly including a locator configured to identify the longitudinal position and the rotational position of the frame assembly during donning, the frame assembly having a first end portion and a second end portion opposite the first end portion, the locator being disposed between the first end portion of the frame assembly and the second end portion of the frame assembly, the locator having a first portion configured to conform to an anatomical protuberance of the limb and a second portion configured to conform to an anatomical recess of the limb, the frame assembly including at least one spring-loaded strip, the strip being radially spring-loaded towards a center of the frame assembly, the frame assembly including a mounting portion configured to removably couple an electrical stimulator thereto such that the electrical stimulator is supported by the frame assembly, the mounting portion being disposed between the locator and the first end portion of the frame assembly; and an electrode base coupled to an inner surface of the frame assembly, the electrode base configured to be coupled to a surface electrode, the electrode base being disposed between the locator and the second end portion of the frame assembly, and the frame assembly configured such that the surface electrode is disposed at a predetermined position overlying a target stimulation point of the limb when the frame assembly substantially envelops the portion of the limb.

18. The apparatus of claim 17, further comprising:
a connector assembly configured to electrically couple the electrical stimulator to the surface electrode, at least a portion of the connector assembly configured to be disposed within a connector opening defined by the frame.

19. The apparatus of claim 17, further comprising:
a fastening strap coupled to the frame assembly, the fastening strap configured to be coupled across an opening defined between the first end portion of the frame assembly and a second end portion of the frame assembly when the frame assembly is donned on the portion of the limb.

20. The apparatus of claim 17, wherein an inner layer of the frame assembly is constructed of a soft material.

21. The apparatus of claim 17, wherein the electrode base has at least a portion of a hook and loop fastener to reversibly couple the surface electrode to the frame assembly.

22. The apparatus of claim 17, wherein the mounting portion is configured to receive at least a portion of the electrical stimulator, the mounting portion includes a connector configured to be matingly coupled to a complementary connector of the electrical stimulator to couple the mounting portion to the electrical stimulator when the portion of the electrical stimulator is received by the mounting portion.

23. The apparatus of claim 17, wherein the mounting portion includes a cradle defining a recess configured to receive the electrical stimulator to couple the mounting portion to the electrical stimulator.

24. The apparatus of claim 17, wherein the frame assembly includes a first orthosis layer and a second orthosis layer.

25. The apparatus of claim 24, wherein the second orthosis layer is removably coupled to the first orthosis layer.

26. The apparatus of claim 24, wherein the first orthosis layer is semi-rigid, the second orthosis layer is constructed of a soft material.

27. The apparatus of claim 17, wherein the locator is a first locator, a first edge portion of the frame assembly between the first end portion of the frame assembly and the second end portion of the frame assembly includes the first locator, the frame assembly including a second locator, a second edge portion of the frame assembly between the first end portion of the frame assembly and the second end portion of the frame assembly includes the second locator, the second edge portion being opposite the first edge portion.

28. The apparatus of claim 17, wherein the predetermined position is adjacent a muscle of the limb such that stimulation of the limb via the surface electrode results in flexion of a foot.

29. The apparatus of claim 17, wherein the predetermined position overlies a motor nerve in the lower leg.

* * * * *